US012649906B2

(12) United States Patent
Thomson et al.

(10) Patent No.: US 12,649,906 B2
(45) Date of Patent: *Jun. 9, 2026

(54) HUMAN PLURIPOTENT STEM CELL-BASED MODELS FOR PREDICTIVE DEVELOPMENTAL NEURAL TOXICITY

(71) Applicant: Wisconsin Alumni Research Foundation, Madison, WI (US)

(72) Inventors: James A. Thomson, Madison, WI (US); William L. Murphy, Waunakee, WI (US); Charles D. Page, Sun Prairie, WI (US); Michael P. Schwartz, Madison, WI (US); Zhonggang Hou, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1025 days.

This patent is subject to a terminal disclaimer.

(21) Appl. No.: 17/373,523

(22) Filed: Jul. 12, 2021

(65) Prior Publication Data

US 2022/0017873 A1 Jan. 20, 2022

Related U.S. Application Data

(63) Continuation of application No. 14/986,363, filed on Dec. 31, 2015, now Pat. No. 11,060,066.

(60) Provisional application No. 62/098,803, filed on Dec. 31, 2014.

(51) Int. Cl.
*C12N 5/071* (2010.01)
*C12N 5/079* (2010.01)
*C12N 5/0793* (2010.01)
*G01N 33/50* (2006.01)
*C12Q 1/6883* (2018.01)

(52) U.S. Cl.
CPC ......... *C12N 5/0697* (2013.01); *C12N 5/0619* (2013.01); *C12N 5/0622* (2013.01); *G01N 33/5058* (2013.01); *C12N 2502/086* (2013.01); *C12N 2502/1358* (2013.01); *C12N 2502/28* (2013.01); *C12N 2503/02* (2013.01); *C12N 2503/04* (2013.01); *C12N 2506/02* (2013.01); *C12N 2533/30* (2013.01); *C12N 2533/90* (2013.01); *C12Q 1/6883* (2013.01); *C12Q 2600/142* (2013.01); *C12Q 2600/158* (2013.01)

(58) Field of Classification Search
CPC .. C12N 5/0697; C12N 5/0619; C12N 5/0622; C12N 2502/086; C12N 2502/1358; C12N 2502/28; C12N 2503/02; C12N 2503/04; C12N 2506/02; C12N 2533/30; C12N 2533/90; G01N 33/5058; C12Q 1/6883; C12Q 2600/142; C12Q 2600/158
See application file for complete search history.

(56) References Cited

U.S. PATENT DOCUMENTS

| | | | |
|---|---|---|---|
| 2005/0277189 A1 | 12/2005 | Temple et al. | |
| 2007/0218460 A1 | 9/2007 | Takami et al. | |
| 2010/0063948 A1 | 3/2010 | Virkar et al. | |
| 2016/0045641 A1 | 2/2016 | Chou et al. | |

FOREIGN PATENT DOCUMENTS

| | | |
|---|---|---|
| JP | 6967452 | 11/2021 |
| WO | WO 01/078003 A1 | 10/2001 |
| WO | WO 03/079286 A1 | 9/2003 |
| WO | WO2005052154 | 6/2007 |
| WO | WO2016109813 | 7/2016 |

OTHER PUBLICATIONS

Caldeira et al. "Microglia change from a reactive to an age-like phenotype with the time in culture." Front Cell Neurosci. Jun. 2, 2014:8:152. (Year: 2014).*
Senju et al. "Characterization of Dendritic Cells and Macrophages Generated by Directed Differentiation from Mouse Induced Pluripotent Stem Cells." Stem Cells, vol. 27, Issue 5, May 2009, pp. 1021-1031 (Year: 2009).*
Shao et al. "Choroid Sprouting Assay: An Ex Vivo Model of Microvascular Angiogenesis."PLoS One. 2013; 8(7): e69552 (Year: 2013).*
Adams, Structure-activity and dose-response relationships in the neural and behavioral teratogenesis of retinoids, Neurotoxicology and Teratology, 15(3), 193-202, 1993.
Ader, et al., Modeling human development in 3D culture, Current Opinion in Cell Biology, 31, 23-28, 2014.
Arnold, et al., The importance of microglia in the development of the vasculature in the central nervous system, Vascular Cell, 5(4), 2013.
Ashburner, et al., Gene Ontology: tool for the unification of biology, Nature Genetics, 25, 25-29, 2000.
Balmer, et al., Epigenetics and transcriptomics to detect adverse drug effects in model systems of human development, Basic & Clinical Pharmacology & Toxicology, 115(1), 59-68, 2014.
Bayatti, et al., A Molecular Neuroanatomical Study of the Developing Human Neocortex from 8 to 17 Postconceptional Weeks Revealing the Early Differentiation of the Subplate and Subventricular Zone, Cereb Cortex, 18(7), 1536-1548, 2008.

(Continued)

*Primary Examiner* — Titilayo Moloye

(74) *Attorney, Agent, or Firm* — McDonnell Boehnen Hulbert & Berghoff LLP

(57) ABSTRACT

The present invention relates to three-dimensional (3D) tissue constructs and methods of using such 3D tissue constructs to screen for neurotoxic agents. In particular, provided herein are methods of producing and using complex, highly uniform human tissue models comprising physiologically relevant human cells, where the tissue models have the degree of sample uniformity and reproducibility required for use in quantitative high-throughput screening applications.

16 Claims, 16 Drawing Sheets
(12 of 16 Drawing Sheet(s) Filed in Color)

Specification includes a Sequence Listing.

(56)                 References Cited

OTHER PUBLICATIONS

Beamish, et al.,"Deciphering the relative roles of matrix metal-loproteinase- and plasmin-mediated matrix degradation during capillary morphogenesis using engineered hydrogels." (Year: 2019).

Bellinger, A strategy for comparing the contributions of environmental chemicals and other risk factors to neurodevelopment of children, Environ. Health Perspect. 120(4), 2012, pp. 501-507.

Brown, et al., Knowledge-Based Analysis of Microarray Gene Expression Data By Using Support Vector Machines, PNAS, Jan. 4, 2000, vol. 97, No. 1, pp. 262-267.

Brustle, et al., Embryonic stem cell-derived glial precursors: a source of myelinating transplants, Science, 285 (5428), 754-756, 1999.

Bystron, et al., Development of the human cerebral cortex: Boulder Committee revisited, Nature Reviews Neuroscience, 9, 110-122, 2008.

Bystron, et al., The first neurons of the human cerebral cortex, Nature Neuroscience, 9, 880-886, 2006.

Chambers, et al., Highly efficient neural conversion of human ES and iPS cells by dual inhibition of SMAD signaling, Nature Biotechnology, 27, 275-280, 2009.

Chen, et al., Chemically defined conditions for human iPS cell derivation and culture, Nature Methods, 8, 242-249, 2011.

Chintawar, S., et al. "Blood-brain barrier promotes differentiation of human fetal neural precursor cells." Stem cells 27.4 (2009): 838-846.

Choi, C., "Cell-Off: Induced Pluripotent Stem Cells Fall Short of Potential Found in Embryonic Version." Scientific American. Published Feb. 11, 2010. retrieved from https://www.scientificamerican.com/article/cell-induced-pluripotent/ (Year: 2010).

Chou, et al., "In vitro modeling of the neurovascular environment by coculturing adult human brain endothelial cells with human neural stem cells." PLoS One. Sep. 4, 2014; 9(9):e106346. (Year: 2014).

Cooper, et al., Teratogen-mediated inhibition of target tissue response to Shh signaling, Science, 280(5369), 1603-1607, 1998.

Cortes, et al., Support-vector networks, Machine Learning, 20(3), 273-297, 1995.

Crofton, et al., Developmental neurotoxicity testing: recommendations for developing alternative methods for the screening and prioritization of chemicals, ALTEX, 28(1), 9-15, 2010.

Dominguez, et al., POU-III transcription factors (Brn1, Brn2, and Oct6) influence neurogenesis, molecular identity, and migratory destination of upper-layer cells of the cerebral cortex, Cereb Cortex, 23(11), 2632-2643, 2013.

Drury, et al., Hydrogels for tissue engineering: scaffold design variables and applications, Biomaterials, 24(24), 4337-4351, 2003.

Duttenhoefer, et al., "3D scaffolds co-seeded with human endothelial progenitor and mesenchymal stem cells: evidence of prevascularisation within 7 days." Eur Cell Mater. Aug. 29, 2013; 26:49-64; (Year: 2013).

Ebert, et al., Induced pluripotent stem cells from a spinal muscular atrophy patient, Nature, 457, 277-280, 2009.

Eiraku, et al., Self-organized formation of polarized cortical tissues from ESCs and its active manipulation by extrinsic signals, Cell Stem Cell, 3(5), 519-532, 2008.

Examiner Proposed Amendments. Mailed Oct. 19, 2020 (Year: 2020).

Fairbanks, et al., A versatile synthetic extracellular matrix mimic via thiol-norbornene photopolymerization, Advanced Materials, 21(48), 5005-5010, 2009.

Ford, et al., "A macroporous hydrogel for the coculture of neural progenitor and endothelial cells to form functional vascular networks in vivo." Proc Natl Acad Sci USA. Feb. 21, 2006; 103(8):2512-7 (Year: 2006).

Furey, et al., Support vector machine classification and validation of cancer tissue samples using microarray expression data, Bioinformatics, 16(10), 906-914, 2000.

Ginhoux, et al., Origin and differentiation of microglia, Front. Cell Neurosci., 7(45), 2013.

Golub, et al., Molecular classification of cancer: class discovery and class prediction by gene expression monitoring, Science, 286(5439), 531-537, 1999.

Grandjean, et al., Developmental neurotoxicity of industrial chemicals, Lancet, 368(9553) 2167-2178, 2006.

Grandjean, et al., Neurobehavioural effects of developmental toxicity, Lancet Neurol. 13, 330-338 (Mar. 2014).

Hansen, et al., Non-epithelial stem cells and cortical interneuron production in the human ganglionic eminences, Nature Neuroscience, 16 1576-1587, 2013.

Hardin, et al., Evaluation of multiple models to distinguish closely related forms of disease using DNA microarray data: an application to multiple myeloma, Statistical Applications in Genetics and Molecular Biology, 3(1), 2004.

Hoffman, Hydrogels for biomedical applications, Advanced Drug Delivery Reviews, 64(supplement), 18-23, 2012.

Hogberg, et al., Toward a 3D model of human brain development for studying gene/environment interactions, Dec. 20, 2013, Stem Cell Research & Therapy 2013, 4 (Suppl 1): S4, XP055259315, pp. 1-7.

Hou, et al., Pluripotent stem cells induced from mouse somatic cells by small-molecule compounds, Stem Cell Research & Therapy, 4(Suppl 1):S12, 2013.

Howden, et al., Genetic correction and analysis of induced pluripotent stem cells from a patient with gyrate atrophy, PNAS, 108(16), 6537-6542, 2011.

Hu, et al., "Neural differentiation of human induced pluripotent stem cells follows developmental principles but with variable potency." Proc Natl Acad Sci USA. Mar. 2, 2010; 107(9):4335-40 (Year: 2010).

Huang, et al., Systematic and integrative analysis of large gene lists using DAVID bioinformatics resources, Nature Protocols, Nature Publishing Group, GB, Jan. 1, 2009, vol. 4, No. 1, pp. 44-57.

Inman, et al., SB-431542 is a potent and specific inhibitor of transforming growth factor-β superfamily type I activin receptor-like kinase (ALK) receptors ALK4, ALK5, and ALK7, Molecular Pharmacology, 62(1), 65-74, 2002.

International Search Report and Written Opinion from PCT/US2015/068315, dated Jun. 24, 2016, 21 pages.

Ip, et al., The Corticofugal Neuron-Associated Genes ROBO1, SRGAP1, and CTIP2 Exhibit an Anterior to Posterior Gradient of Expression in Early Fetal Human Neocortex Development, Cereb Cortex, 21(6), 1395-1407, 2011.

James, et al., Neuronal action on the developing blood vessel pattern, Seminars in Cell & Developmental Biology, 22 (9), 1019-1027, 2011.

Kadoshima, et al., Self-organization of axial polarity, inside-out layer pattern, and species-specific progenitor dynamics in human ES cell-derived neocortex, PNAS, 110(50), 20284-20289, 2013.

Kettenmann, et al., Physiology of microglia, Physiological Reviews, 91(2), 461-553, 2011.

Kleinstreuer, et al., Phenotypic screening of the ToxCast chemical library to classify toxic and therapeutic mechanisms, Nature Biotechnology, 32, 583-591, 2014.

Kolbe, et al., "Paracrine effects influenced by cell culture medium and consequences on microvessel-like structures in cocultures of mesenchymal stem cells and outgrowth endothelial cells." Tissue Eng Part A. Sep. 2011; 17 (17-18):2199-212. (Year: 2011).

Kusuma, et al., Self-organized vascular networks from human pluripotent stem cells in a synthetic matrix, PNAS, 110 (31), 12601-12606, 2013.

Lancaster, et al., Cerebral organoids model human brain development and microcephaly, Nature, 2013, vol. 501 No. 7467, 18 pages.

Lancaster, et al., Generation of cerebral organoids from human pluripotent stem cells, Nature Protocols, vol. 9, No. 10, Sep. 4, 2014, pp. 2329-2340.

Lancaster, et al., Organogenesis in a dish: modeling development and disease using organoid technologies, Science, 345(6194), 2014.

Langmead, et al., Ultrafast and memory-efficient alignment of short DNA sequences to the human genome, Genome Biology, 10:R25, 2009.

(56) References Cited

OTHER PUBLICATIONS

Leng, et al., EBSeq: an empirical Bayes hierarchical model for inference in RNA-seq experiments, Bioinformatics, 29 (8), 1035-1043, 2013.

Levesque, et al., Synthesis of cell-adhesive dextran hydrogels and macroporous scaffolds, Biomaterials, 27(30), 5277-5285, 2006.

Li, et al., Coordination of sonic hedgehog and Wnt signaling determines ventral and dorsal telencephalic neuron types from human embryonic stem cells, Development, 136, 4055-4063, 2009.

Li, et al., RSEM: accurate transcript quantification from RNA-Seq data with or without a reference genome, BMC Bioinformatics, 12(323), 2011.

Li, X., et al., "Functional hydrogels with tunable structures and properties for tissue engineering applications." Frontiers In chemistry 6 (2018): 499.

Liu, et al., Development and evolution of the human neocortex, Cell, 146(1) 18-36, 2011.

Mariani, et al., Modeling human cortical development in vitro using induced pluripotent stem cells, PNAS, 109(31), 12770-12775, 2012.

Marin-Padilla, et al., Developmental Aspects of the Intracerebral Microvasculature and Perivascular Spaces: Insights into Brain Response to Late-Life Diseases, J Neuropathol Exp Neurol, 70(12), 1060-1069, 2011.

Marin-Padilla, The human brain intracerebral microvascular system: development and structure, Front. Neuroanat. 9(38), 2012.

Meyer, et al., Embryonic and early fetal development of the human neocortex, Journal of Neuroscience, 20(5), 1858-1868, 2000.

Molyneaux, et al., Neuronal subtype specification in the cerebral cortex, Nature Reviews Neuroscience, 8, 427-437, 2007.

Monier, et al., Distribution and differentiation of microglia in the human encephalon during the first two trimesters of gestation, Journal of Comparative Neurology, 499(4), 565-582.

Monier, et al., Entry and distribution of microglial cells in human embryonic and fetal cerebral cortex, J Neurophathol Exp Neurol, 66(5), 372-382, 2007.

Montano, et al., Formation of human capillaries in vitro: the engineering of prevascularized matrices, Tissue Engineering Part A, 16(1), 269-282, 2009.

Montgomery, et al., Engineering personalized neural tissue by combining induced pluripotent stem cells with fibrin scaffolds, Biomaterials Science, vol. 3, No. 2, 2015, pp. 401-413.

Moon, et al., "Biomimetic hydrogels with pro-angiogenic properties." Biomaterials. May 2010; 31(14):3840-7 (Year: 2010).

Moors, et al., Human neurospheres as three-dimensional cellular systems for developmental neurotoxicity testing, Environmental Health Perspectives, 117(7), 1131-1138, 2009.

Nagase, et al., Human matrix metalloproteinase specificity studies using collagen sequence-based synthetic peptides, Biopolymers, 40(4), 399-416, 1996.

Needham, et al., Partition of environmental chemicals between maternal and fetal blood and tissues, Environ. Sci. Technol. 45(3), 1121-1126 2011.

Nguyen, et al., Photopolymerizable hydrogels for tissue engineering applications, Biomaterials, 23(22), 4307-4314, 2002.

Olson, et al., Concordance of the toxicity of pharmaceuticals in humans and in animals, Regulatory Toxicology and Pharmacology, 32(1), 56-67, 2000.

Pellett, S., et al., Human Induced Pluripotent Stem Cell Derived Neuronal Cells Cultured on Chemically-Defined Hydrogels for Sensitive In Vitro Detection of Botulinum Neurotoxin, Sci. Rep. 5, 14566; doi: 10.1038/srep14566 (2015).

Pierschbacher, et al., Cell attachment activity of fibronectin can be duplicated by small synthetic fragments of the molecule, Nature, 309(5963), 30-33, 1984.

Radio, et al., Comparison of PC12 and cerebellar granule cell cultures for evaluating neurite outgrowth using high content analysis, Neurotoxicology and Teratology, 32(1), 25-35, 2010.

Rakic, Developmental and evolutionary adaptations of cortical radial glia, Cereb Cortex, 13(6), 541-549, 2003.

Rakic, Emerging complexity of layer I in human cerebral cortex, Cereb Cortex, 13(10), 1072-1083, 2003.

Rakic, Evolution of the neocortex: perspective from developmental biology, Nature Reviews Neuroscience, 10, 724-735, 2009.

Rice, D., et al., "Critical periods of vulnerability for the developing nervous system: evidence from humans and animal models." Environmental health perspectives 108.suppl 3 (2000): 511-533.

Saito, et al., Neocortical layer formation of human developing brains and lissencephalies: consideration of layer-specific marker expression, Cereb Cortex, 21(3), 588-596, 2011.

Schwartz, et al., Human pluripotent stem cell-derived neural constructs for predicting neural toxicity, PNAS, Sep. 21, 2015, vol. 112, No. 40, including supporting information, 37 pages.

Seliktar, et al., "MMP-2 sensitive, VEGF-bearing bioactive hydrogels for promotion of vascular healing." J Biomed Mater Res A. Mar. 15, 2004;68(4):704-16 (Year: 2004).

Shu, X. Z., et al., "Attachment and spreading of fibroblasts on an RGD peptide-modified injectable hyaluronan hydrogel." Journal of Biomedical Materials Research Part A. 68.2 (2004): 365-375.

Singec, et al., Defining the actual sensitivity and specificity of the neurosphere assay in stem cell biology, Nature Methods, 3, 801-806, 2006.

Smirnova, et al., Food for Thought: Developmental Neurotoxicity—Challenges in the 21st Century and In Vitro Opportunities, ALTEX-Altern. Anim. Exp. 31(2), 129-156 (2014).

Stewart, et al., Comparative RNA-seq analysis in the unsequenced axolotl: the oncogene burst highlights early gene expression in the blastema, PLOS Computational Biology, 9(3), e1002936, 2013.

Struyf, et al., Combining gene expression, demographic and clinical data in modeling disease: a case study of bipolar disorder and schizophrenia, BMC Genomics, 9(531), 2008.

Sun, et al., "Co-culture of outgrowth endothelial cells with human mesenchymal stem cells in silk fibroin hydrogels promotes angiogenesis." Biomed Mater. Jun. 7, 2016;11(3):035009. (Year: 2016).

Takahashi, et al., Induction of pluripotent stem cells from adult human fibroblasts by defined factors, Cell, 131(5), 861-872, 2007.

Thomson, et al., Embryonic stem cell lines derived from human blastocysts, Science, 282(5391), 1145-1147, 1998.

Turturro, et al., "MMP-sensitive PEG diacrylate hydrogels with spatial variations in matrix properties stimulate directional vascular sprout formation." PLoS One. 2013;8(3):e58897 (Year: 2013).

Uenishi, et al., Tenascin C promotes hematoendothelial development and T lymphoid commitment from human pluripotent stem cells in chemically defined conditions, Stem Cell Reports, 3(6), 1073-1084, 2014.

Verney, et al., Early microglial colonization of the human forebrain and possible involvement in periventricular white-matter injury of preterm infants, Journal of Anatomy, 271(4), 436-448, 2010.

Wilson, et al., Multiparametric High Content Analysis for assessment of neurotoxicity in differentiated neuronal cell ines and human embryonic stem cell-derived neurons, NeuroToxicology, 42, 33-48, 2014.

Yu, et al., Human induced pluripotent stem cells free of vector and transgene sequences, Science, 324 (5928), 797-801, 2009.

Yu, et al., Induced pluripotent stem cell lines derived from human somatic cells, Science, 318(5858), 1917-1920, 2007.

Zecevic, et al., Early development and composition of the human primordial plexiform layer: an immunohistochemical study, Journal of Comparative Neurology, 412(2), 241-254, 1999.

Zhang, et al., In vitro differentiation of transplantable neural precursors from human embryonic stem cells, Nature Biotechology, 19, 1129-1133, 2001.

Lippmann et al., "Modeling the blood-brain barrier using stem cell sources", Fluids Barriers of the CNS., 10(1), Article 2, pp. 1-14, (2013).

* cited by examiner

FIGS. 1A-1B, CONTINUED
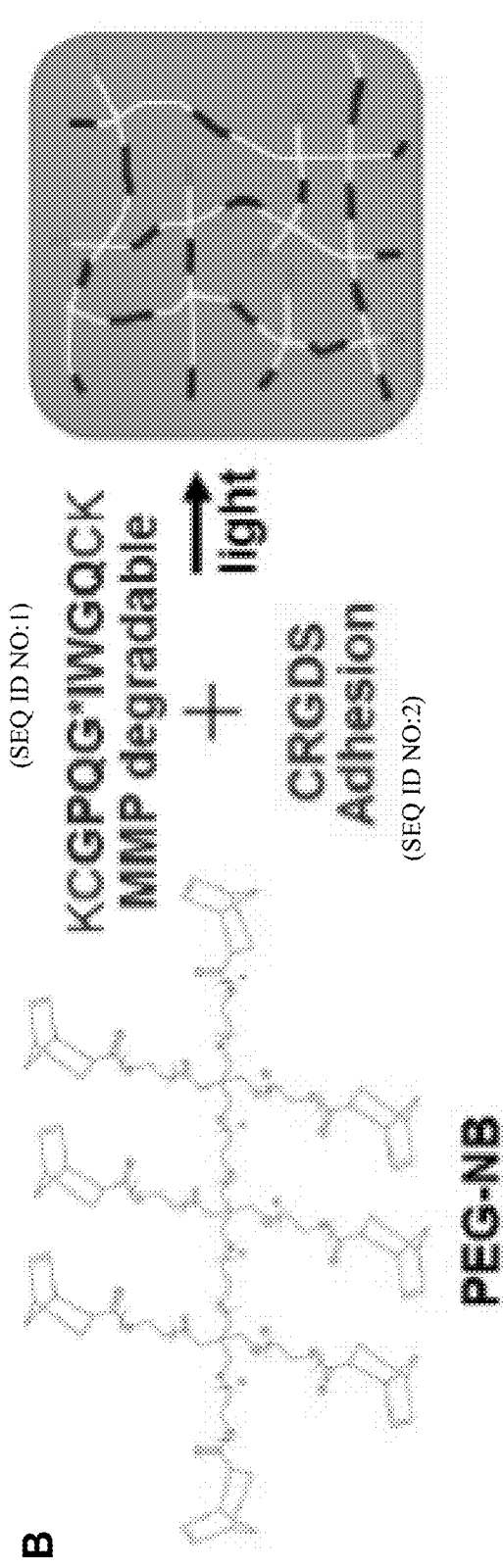
KCGPQG*IWGQCK
MMP degradable
(SEQ ID NO:1)
+
CRGDS
Adhesion
(SEQ ID NO:2)
light
PEG-NB
B FIGS. 2A-2D, CONTINUED
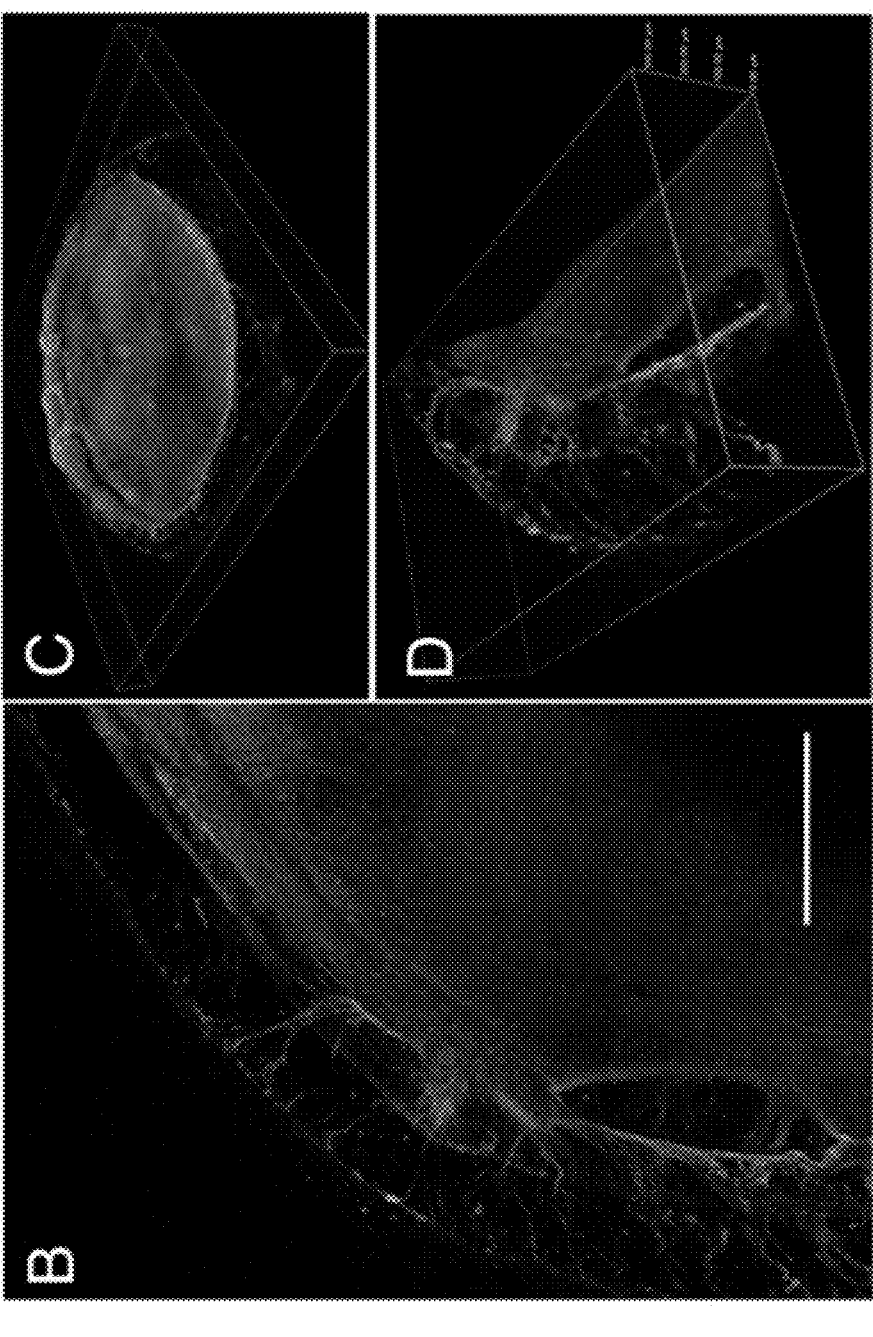

FIGS. 4A-4K

FIGS. 4A-4K, CONTINUED

FIGS. 6A-6B, CONTINUED
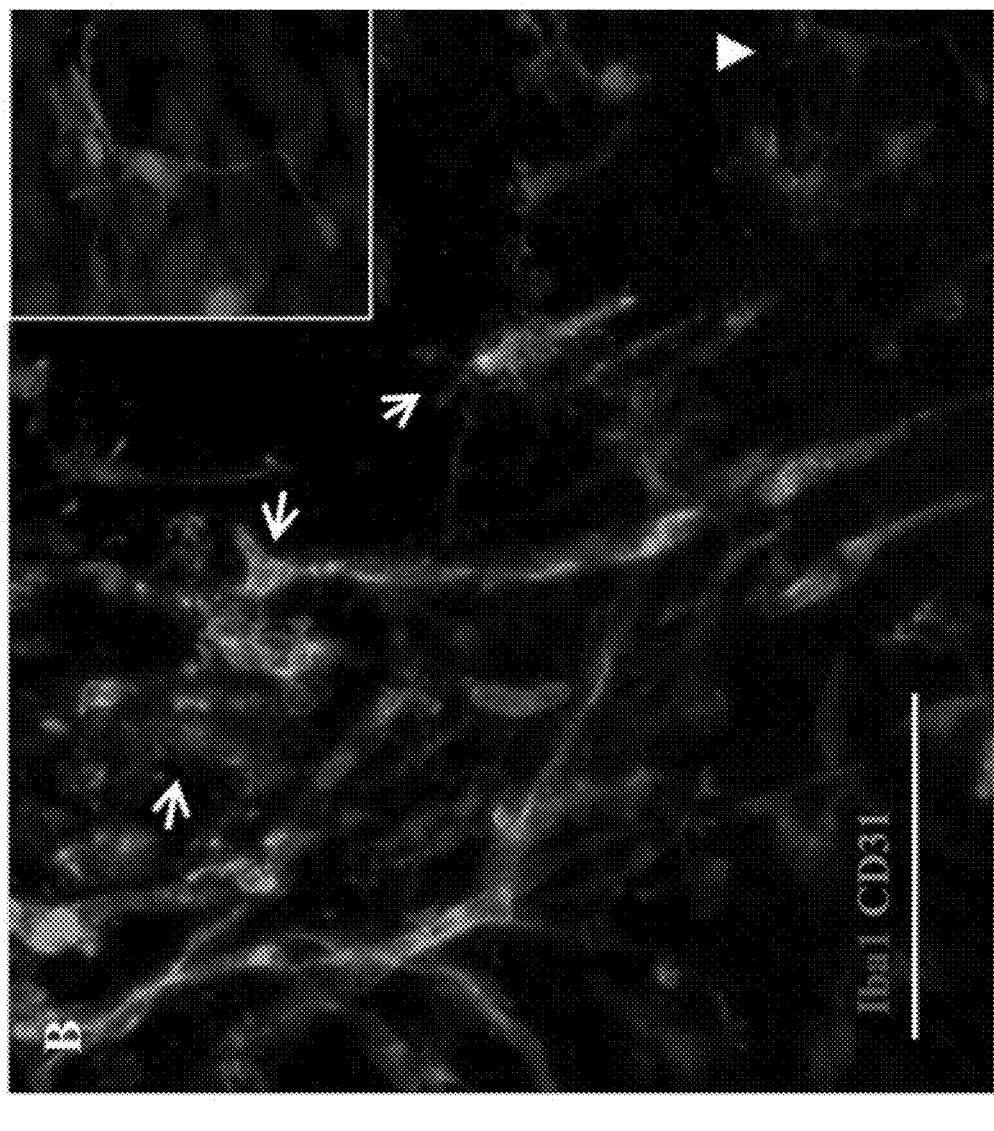

FIG. 8

| Microglia | Day 16 | Day 21 | Day 16 | Day 21 |
|---|---|---|---|---|
| AIF1 (Iba1) | 12.1 ± 3.1 | 15.6± 8.8 | 3.3 | 8.8 |
| ITGAM | 2.3 ± 0.8 | 1.2 ± 1.2 | 0.6 | 1.2 |
| PTPRC | 4.1 ± 0.9 | 3.6 ± 3.3 | 0.9 | 3.3 |
| CX3CR1 | 3.8 ± 0.8 | 3.7 ± 4.0 | 0.8 | 4.6 |
| CD68 | 17.3 ± 4.0 | 23.8 ± 18 | 4.0 | 18.9 |
| CD14 | 1.8 ± 1.6 | 3.0 ± 1.4 | 1.6 | 1.4 |
| CD4 | 3.8 ± 0.9 | 3.2 ± 2.0 | 0.9 | 2.0 |
| TREM2 | 6.7 ± 2.2 | 7.0 ± 5.0 | 2.2 | 5.0 |

| Synapse, etc. | Day 16 | Day 21 | Day 16 | Day 21 |
|---|---|---|---|---|
| SNAP25 | 95.3 | 112.3 | 5.0 | 23.2 |
| SV2A | 90.9 | 77.1 | 3.4 | 7.0 |
| SV2B | 2.2 | 3.4 | 0.3 | 1.4 |
| SV2C | 10.5 | 4.1 | 2.2 | 2.3 |

| Cortical Differentiation | Day 16 | Day 21 | Day 16 | Day 21 |
|---|---|---|---|---|
| RELN | 72.9 | 45.1 | 1.4 | 7.4 |
| CUX1 | 54.0 | 54.0 | 6.6 | 4.5 |
| CUX2 | 18.7 | 14.6 | 1.5 | 3.1 |
| POU3F2 (Brn2) | 160.9 | 122.6 | 9.7 | 22.3 |
| SATB2 | 10.1 | 8.3 | 0.8 | 3.2 |
| BCL11B (Ctip2) | 37.4 | 34.1 | 4.0 | 10.6 |
| SOX2 | 138.5 | 100.7 | 5.1 | 31.4 |
| EOMES | 1.8 | 2.2 | 0.6 | 1.7 |
| PAX6 | 3.7 | 2.6 | 0.5 | 1.3 |
| NEUROG2 | 71.7 | 56.6 | 8.0 | 8.0 |

| Blood Vessel | Day 16 | Day 21 | Day 16 | Day 21 |
|---|---|---|---|---|
| PECAM1 | 1.4 | 1.7 | 0.3 | 0.3 |
| KDR | 9.2 | 8.7 | 2.1 | 6.8 |
| MCAM | 15.7 | 23.8 | 2.4 | 1.8 |
| AQP4 | 64.6 | 52.8 | 2.9 | 14.0 |

FIG. 9

| 100K NPC + EC + MSC | | Day 14 | | | | | | | | Day 21 | | | | | | | |
|---|---|---|---|---|---|---|---|---|---|---|---|---|---|---|---|---|---|
| | | No Microglia | | | | With Microglia | | | | No Microglia | | | | With Microglia | | | |
| | | MSC media 1 | MSC media 2 | Pc Media 1 | Pc Media 2 | MSC media 1 | MSC media 2 | Pc Media 1 | Pc Media 2 | MSC media 1 | MSC media 2 | Pc Media 1 | Pc Media 2 | MSC media 1 | MSC media 2 | Pc Media 1 | Pc Media 2 |
| Day 14 (-MG) | MSC media 1 | 1 | 0.99 | 0.99 | 0.99 | 0.98 | 0.98 | 0.98 | 0.98 | 0.99 | 0.99 | 0.98 | 0.99 | 0.98 | 0.98 | 0.98 | 0.98 |
| | MSC media 2 | 0.99 | 1 | 0.99 | 0.99 | 0.98 | 0.98 | 0.98 | 0.98 | 0.99 | 1 | 0.99 | 0.99 | 0.98 | 0.98 | 0.98 | 0.98 |
| | Pc Media 1 | 0.99 | 0.99 | 1 | 0.99 | 0.98 | 0.98 | 0.98 | 0.98 | 0.99 | 0.99 | 0.98 | 0.99 | 0.98 | 0.98 | 0.98 | 0.98 |
| | Pc Media 2 | 0.99 | 0.99 | 0.99 | 1 | 0.98 | 0.97 | 0.98 | 0.98 | 0.99 | 0.99 | 0.99 | 0.98 | 0.98 | 0.98 | 0.98 | 0.98 |
| Day 21 (+MG) | MSC media 1 | 0.98 | 0.96 | 0.98 | 0.97 | 1 | 0.99 | 1 | 0.99 | 0.97 | 0.99 | 0.97 | 0.97 | 0.98 | 0.98 | 0.98 | 0.98 |
| | MSC media 2 | 0.98 | 0.96 | 0.98 | 0.97 | 0.99 | 1 | 0.99 | 0.99 | 0.97 | 0.97 | 0.97 | 0.97 | 0.98 | 0.98 | 0.98 | 0.98 |
| | Pc Media 1 | 0.98 | 0.98 | 0.98 | 0.98 | 0.99 | 0.99 | 1 | 0.99 | 0.97 | 0.97 | 0.97 | 0.97 | 0.98 | 0.98 | 0.98 | 0.98 |
| | Pc Media 2 | 0.98 | 0.98 | 0.98 | 0.98 | 0.99 | 0.99 | 0.99 | 1 | 0.97 | 0.97 | 0.97 | 0.97 | 0.98 | 0.98 | 0.98 | 0.98 |
| Day 21 (-MG) | MSC media 1 | 0.99 | 0.99 | 0.99 | 0.99 | 0.97 | 0.97 | 0.97 | 0.97 | 1 | 0.99 | 0.99 | 0.99 | 0.98 | 0.98 | 0.98 | 0.98 |
| | MSC media 2 | 0.99 | 0.99 | 0.99 | 0.99 | 0.97 | 0.97 | 0.97 | 0.97 | 0.99 | 1 | 0.99 | 0.99 | 0.98 | 0.98 | 0.98 | 0.98 |
| | Pc Media 1 | 0.98 | 0.99 | 0.98 | 0.99 | 0.97 | 0.97 | 0.97 | 0.97 | 0.99 | 0.99 | 1 | 0.99 | 0.98 | 0.98 | 0.98 | 0.98 |
| | Pc Media 2 | 0.99 | 0.99 | 0.99 | 0.98 | 0.97 | 0.97 | 0.97 | 0.97 | 0.99 | 0.99 | 0.99 | 1 | 0.98 | 0.98 | 0.98 | 0.98 |
| Day 21 (+MG) | MSC media 1 | 0.98 | 0.98 | 0.98 | 0.98 | 0.98 | 0.98 | 0.98 | 0.98 | 0.98 | 0.98 | 0.98 | 0.98 | 1 | 0.99 | 0.99 | 0.99 |
| | MSC media 2 | 0.98 | 0.98 | 0.98 | 0.98 | 0.98 | 0.98 | 0.98 | 0.98 | 0.98 | 0.98 | 0.98 | 0.98 | 0.99 | 1 | 0.99 | 0.99 |
| | Pc Media 1 | 0.98 | 0.98 | 0.98 | 0.98 | 0.98 | 0.98 | 0.98 | 0.98 | 0.98 | 0.98 | 0.98 | 0.98 | 0.99 | 0.99 | 1 | 0.99 |
| | Pc Media 2 | 0.98 | 0.98 | 0.98 | 0.98 | 0.98 | 0.98 | 0.98 | 0.98 | 0.98 | 0.98 | 0.98 | 0.98 | 0.99 | 0.99 | 0.99 | 1 |

FIGS. 10A-10E, CONTINUED
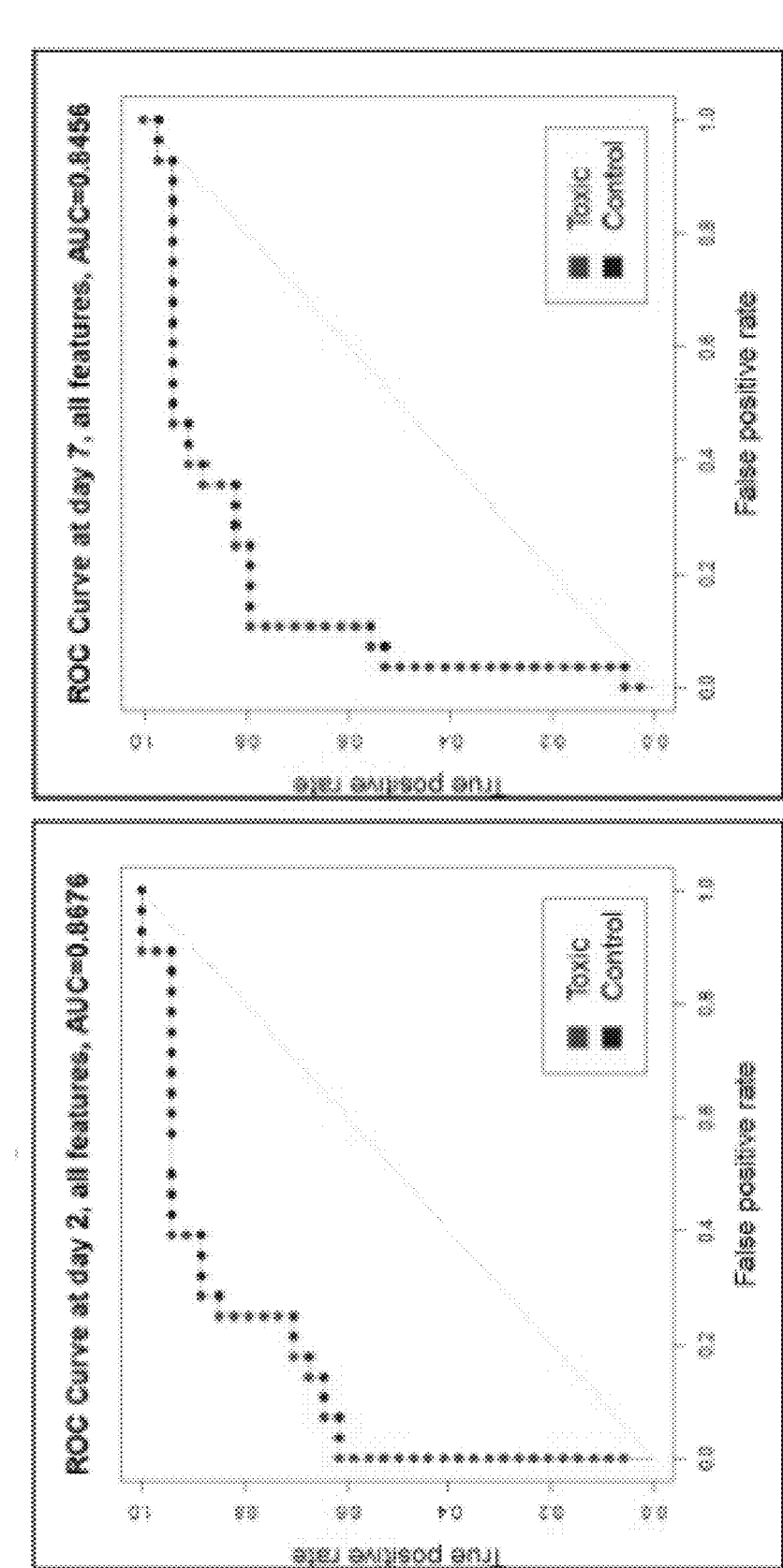

List of chemicals tested

| Toxins | | | Controls | | | Blinded |
|---|---|---|---|---|---|---|
| Accutane | Dexamethasone | Lydocainhane | Acetaminophen | estrogen | sucrose | PenStrep |
| Amiodarone | diazinon | maneb | ampicillin | etidronate | tamoxifen | |
| amphen | Dieca | monosodium glutamate | none | 4-hydroxy-tamoxifen HCl | | anthrone | maltose |
| Arsenic | 5-Fluorouracil | Okadaic acid | 17 beta-estradiol | lovastatin | | lactose | Oleic acid |
| benzene | GDC-0449 | PD98059 | Carbenicillin | Meropenem | | |
| bexaloten | hydroxyurea | permethrin | Cefepime | Neporomos sodium | | |
| Bu-1 | 2-hydroxyestradiol | propylthiouracil | DMSO | PEG 3350 | | |
| BMAA | K252a | (trans) Retinoic acid | Doxycycline | PVP | | |
| Busulfan | kainate | Thalidomide | Bcl2400 | Resveratrol | | |
| Cadmium | LDE225 | U0126 | fructose | succhose | | |
| Carbamazepine | lead acetate | Vincristine | glucosamine | sorbitol | | |
| Cytosine β-D-arabinofuranoside | | | glycerol | | | |
| cyclopamine | L-741828 | PD0325901 | | | | |
| GBR 12909 | Ouabain | | | | | |

SEQUENCE LISTING

```
<160> NUMBER OF SEQ ID NOS: 13

<210> SEQ ID NO 1
<211> LENGTH: 12
<212> TYPE: PRT
<213> ORGANISM: Artificial Sequence
<220> FEATURE:
<223> OTHER INFORMATION: synthetic

<400> SEQUENCE: 1

Lys Cys Gly Pro Gln Gly Ile Trp Gly Gln Cys Lys
1               5                   10

<210> SEQ ID NO 2
<211> LENGTH: 5
<212> TYPE: PRT
<213> ORGANISM: Artificial Sequence
<220> FEATURE:
<223> OTHER INFORMATION: synthetic

<400> SEQUENCE: 2

Cys Arg Gly Asp Ser
1               5

<210> SEQ ID NO 3
<211> LENGTH: 27
<212> TYPE: DNA
<213> ORGANISM: Artificial Sequence
<220> FEATURE:
<223> OTHER INFORMATION: synthetic
<220> FEATURE:
```

```
<221> NAME/KEY: misc_feature
<222> LOCATION: (22)..(27)
<223> OTHER INFORMATION: n is a, c, g, t or u

<400> SEQUENCE: 3
ccttggcacc cgagaattcc annnnnn                                        27

<210> SEQ ID NO 4
<211> LENGTH: 34
<212> TYPE: DNA
<213> ORGANISM: Artificial Sequence
<220> FEATURE:
<223> OTHER INFORMATION: synthetic

<400> SEQUENCE: 4
agatcggaag agcgtcgtgt agggaaagag tgtc                                34

<210> SEQ ID NO 5
<211> LENGTH: 58
<212> TYPE: DNA
<213> ORGANISM: Artificial Sequence
<220> FEATURE:
<223> OTHER INFORMATION: synthetic

<400> SEQUENCE: 5
aatgatacgg cgaccaccga gatctacact ctttccctac acgacgctct tccgatct     58

<210> SEQ ID NO 6
<211> LENGTH: 67
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (25)..(34)
<223> OTHER INFORMATION: n is a, c, g, or t

<400> SEQUENCE: 6
caagcagaag acggcatacg agatnnnnnn nnnngtgact ggagttcctt ggcacccgag   60
aattcca                                                             67

<210> SEQ ID NO 7
<211> LENGTH: 4
<212> TYPE: PRT
<213> ORGANISM: Artificial Sequence
<220> FEATURE:
<223> OTHER INFORMATION: synthetic

<400> SEQUENCE: 7

Arg Gly Asp Ser
1

<210> SEQ ID NO 8
<211> LENGTH: 5
<212> TYPE: PRT
<213> ORGANISM: Artificial Sequence
<220> FEATURE:
<223> OTHER INFORMATION: synthetic

<400> SEQUENCE: 8

Arg Gly Asp Ser Cys
1               5

<210> SEQ ID NO 9
<211> LENGTH: 6
```

```
<212> TYPE: PRT
<213> ORGANISM: Artificial Sequence
<220> FEATURE:
<223> OTHER INFORMATION: synthetic

<400> SEQUENCE: 9

Cys Cys Arg Gly Asp Ser
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic

<400> SEQUENCE: 10

Cys Cys Cys Arg Gly Asp
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 11

Cys Arg Gly Asp Ser
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: C-terminal CONH2

<400> SEQUENCE: 12

Cys Arg Gly Asp Ser
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: C-terminal CONH2

<400> SEQUENCE: 13

Cys Arg Gly Asp Ser
1               5
```

HUMAN PLURIPOTENT STEM CELL-BASED MODELS FOR PREDICTIVE DEVELOPMENTAL NEURAL TOXICITY

CROSS-REFERENCE TO RELATED APPLICATIONS

This application is a divisional of U.S. application Ser. No. 14/986,363, filed Dec. 31, 2015, which claims the benefit of U.S. Application Ser. No. 62/098,803, filed Dec. 31, 2014, each of which is incorporated herein as if set forth in its entirety.

STATEMENT REGARDING FEDERALLY FUNDED RESEARCH OR DEVELOPMENT

This invention was made with government support under TR000506 awarded by the National Institutes of Health. The government has certain rights in the invention.

BACKGROUND

Pluripotent stem cells offer a potentially powerful tool for improving in vitro models and investigating the underlying mechanisms of development of human neural tissue and of neurotoxicity. Animal models have provided insight into mechanisms of neurodevelopment, but are of limited value for predicting developmental neurotoxicity due to poorly understood differences in the human brain such as an expanded cerebral cortex. Thus, there remains a need for models that recapitulate complex human tissues and biological processes and that are suitable for screening potentially hazardous compounds. Furthermore, there remains a need in the art for efficient, reproducible, and xenogeneic material-free methods for producing three-dimensional tissue constructs including neural tissue constructs having high uniformity for standardized quantitative and qualitative assessments and for predictive analysis of candidate neurotoxic agents.

SUMMARY

In a first aspect, the present invention provides a method of producing a vascularized neural tissue construct. The method comprises or consists essentially of (a) seeding a three-dimensional porous biomaterial with human neural progenitor cells; (b) culturing the seeded biomaterial for a length of time sufficient to detect differentiation of at least a portion of the neural progenitor cells; (c) dispersing on or within the cultured seeded biomaterial at least one human cell type selected from the group consisting of endothelial cells, mesenchymal cells, primitive macrophages, and pericytes; and (d) culturing the seeded biomaterial comprising the at least one dispersed human cell type under culture conditions that promote cell differentiation, whereby a vascularized neural tissue construct comprising human neurons and glial cells is produced. The three-dimensional porous biomaterial can be a hydrogel. The hydrogel can comprise polymerized poly(ethylene glycol) (PEG) or polymerized polysaccharide. The at least one dispersed human cell type can be derived from a human pluripotent stem cell. The human pluripotent stem cell can be an embryonic stem cell or an induced pluripotent stem cell. In some cases, the at least one dispersed human cell type comprises human pluripotent stem cell-derived primitive macrophages and the 3D vascularized neural tissue construct further comprises mature microglia. Seeding the porous biomaterial can comprise contacting to the porous biomaterial at least one human neural progenitor cell.

In some cases, the method further comprises dispersing within or on the porous biomaterial a bioactive agent that modulates a morphological feature, function, or differentiation status of a cell seeded or dispersed therein. The bioactive agent can be selected from the group consisting of a growth factor, a cytokine, and a bioactive peptide, or a combination thereof. The vascularized neural tissue construct can exhibit one or more properties selected from the group consisting of: (i) an interconnected vasculature; (ii) differentiated cells within the neural tissue construct mutually contact each other in three dimensions; (iii) more than one layer of cells; and (iv) a function or property characteristic of human neural tissue in vivo or in situ. In some cases, the neurons and glial cells are selected from the group consisting of GABAergic neurons, glutamatergic neurons, astrocytes, and oligodendrocytes. The porous biomaterial can be degradable. The degradable hydrogel can be selected from the group consisting of an enzymatically degradable hydrogel, a hydrolytically degradable hydrogel, or a photodegradable hydrogel. The enzymatically degradable hydrogel can be matrix metalloproteinase (MMP)-degradable.

In another aspect, provided herein is a three-dimensional (3D) vascularized neural tissue construct obtained according to a method described herein. The neural tissue construct can comprise mature microglia. The neural tissue construct can comprise stratified layers of neurons and glia.

In a further aspect, provided herein is a method of in vitro screening of an agent. The method comprises or consists essentially of (a) contacting a test agent to a vascularized neural tissue construct obtained according to the method of claim 1; and (b) detecting an effect of the agent on one or more cell types within the contacted neural tissue construct. The agent can be screened for toxicity to human neural tissue. In some cases, detecting comprises detecting at least one effect of the agent on morphology or life span of cells or tissues within the contacted tissue construct, whereby an agent that reduces the life span of the cells or tissues or has a negative impact on the morphology of the cells or tissues is identified as toxic to human neural tissue. In some cases, detecting comprises performing a method selected from the group consisting of RNA sequencing, gene expression profiling, transcriptome analysis, metabolome analysis, detecting reporter or sensor, protein expression profiling, Forster resonance energy transfer (FRET), metabolic profiling, and microdialysis. The agent can be screened for an effect on gene expression, and detecting can comprise assaying for differential gene expression relative an uncontacted tissue construct.

In some cases, the method further comprises using a predictive model to determine the relationship of gene expression levels of a panel of markers for the test compound-contacted tissue construct to gene expression levels of markers that are characteristic of exposure to a neurotoxic agent, where the predictive model is constructed using transcription and metabolic profiles obtained for each component of a panel of agents having known neurotoxic effects as markers of toxicity to human neural tissue.

In another aspect, provided herein is a tissue construct screening system. The system comprises or consists essentially of an analytical device configured to obtain data comprising measurements from a human vascularized neural tissue construct; a computer controller configured to receive the data from the analytical device; and a machine-based adaptive learning system trained using known gene expression data and configured to select a subset of features from the data using a feature selection algorithm, where the subset of features correspond to a change in a level of expression of at least one gene following exposure to a known or unknown compound. The human vascularized neural tissue construct can be obtained according to a method described herein. Measurements can comprise gene expression data obtained from microarray analysis.

In yet another aspect, provided herein is use of a three-dimensional human vascularized neural tissue construct obtained according to a method described herein in a drug discovery or toxicity screen.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

INCORPORATION BY REFERENCE

All publications, patents, and patent applications mentioned in this specification are herein incorporated by reference to the same extent as if each individual publication, patent, and patent application was specifically and individually indicated to be incorporated by reference.

This application includes a sequence listing in computer readable form (a "txt" file) that is submitted herewith. This sequence listing is incorporated by reference herein.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein:

FIGS. 2A-2D demonstrates the influence of hydrogel properties on spreading for mesenchymal stem cells (MSCs) cultured in PEG hydrogels formed via thiol-ene photopolymerization. The images in FIGS. 2A-2D illustrate PEG hydrogels that incorporate CRGDS for cellular adhesion and MMP-crosslinking peptides that are derived from a native collagen sequence (ALA) or which have been engineered to enhance degradation rate (TRYP and LEU). Matrix remodeling can be tuned by controlling biological properties of the synthetic matrix. Mesenchymal stem cell (MSC) spreading is a function of degradation rate and adhesion ligand density. MSC attachment and spreading was tuned by varying adhesion ligand density (using the fibronectin mimic CRGDS) or the susceptibility of the crosslinker to proteolytic degradation (by varying the P'$_2$ position of the amino acid sequence). (A) MSC spreading was maximized with Tryptophan in the P'$_2$ position of the amino acid sequence and 1000 mM RGD. (B) MSCs remained rounded in hydrogels with the most degradable crosslinker (Tryptophan in the P'$_2$ position), but without active adhesion peptide (0 RGD condition, RGD replaced with non-bioactive RDG scrambled peptide). (C) Only limited spreading was observed when Tryptophan was replaced with Ala due to lower susceptibility to MMP degradation while (D) intermediate spreading was observed when Tryptophan was replaced with Leu. (E, F) Live/dead staining demonstrates that human umbilical vein endothelial cells (HUVECs) are viable when grown in 3D synthetic extracellular matrices with two different RGD concentrations which leads to differences in 3D organization. (G) Images of human dermal fibroblasts grown in 3D synthetic matrix compared to (H) collagen reveal that basic cell morphologies and cytoskeletal structure are indistinguishable between them (where gels are matched for mechanical properties). (I) Modulus (stiffness) can be varied across a wide range of values by choice of monomer density (wt %), molecular weight, and PEG backbone molecule (4-arm or 8-arm).

FIGS. 4A-4K are confocal images demonstrating that neural tissue constructs are characterized by neurons with diverse morphologies and long-range order. Immunofluorescence imaging reveals neuronal and glial phenotypes. (A-E) Maximum projection immunofluorescence images illustrating βIII-tubulin (green) and DAPI (blue) expression for full vascularized neural construct formed within a 24-well transwell insert (top left). (F-J) Distinct neuronal phenotypes. (F) Calretinin (green) and Reelin (red). (G-K) βIII-tubulin (red) coexpressed with (G) GABA, (H) VGLUT2, (I) FOXG1, (J) Ctip2, and (K) Brn2. Scale bars: 100 μm (F-K).

5 with or without microglia (Quality Control Experiments; N.D., not detected). Statistical analysis was conducted using a Student's t test (TPM±SD; ***P<0.001; n=4 replicate samples each). (B) Immunofluorescence images showing Iba1 (microglia, red) and CD31 (endothelial cells, green) expression for a day 21 neural construct. Microglia adopt ramified morphologies (e.g., closed arrow) and associate with capillary tubules (e.g., open arrows). (Inset) Iba1 (red) and DAPI (blue) expression for the cell pointed out by the closed arrow (Bottom, Right corner) and surrounding nuclei. Image is brightened for clarity. (Scale bar, 100 μm.)

Figures 7A, 7B, 7C:
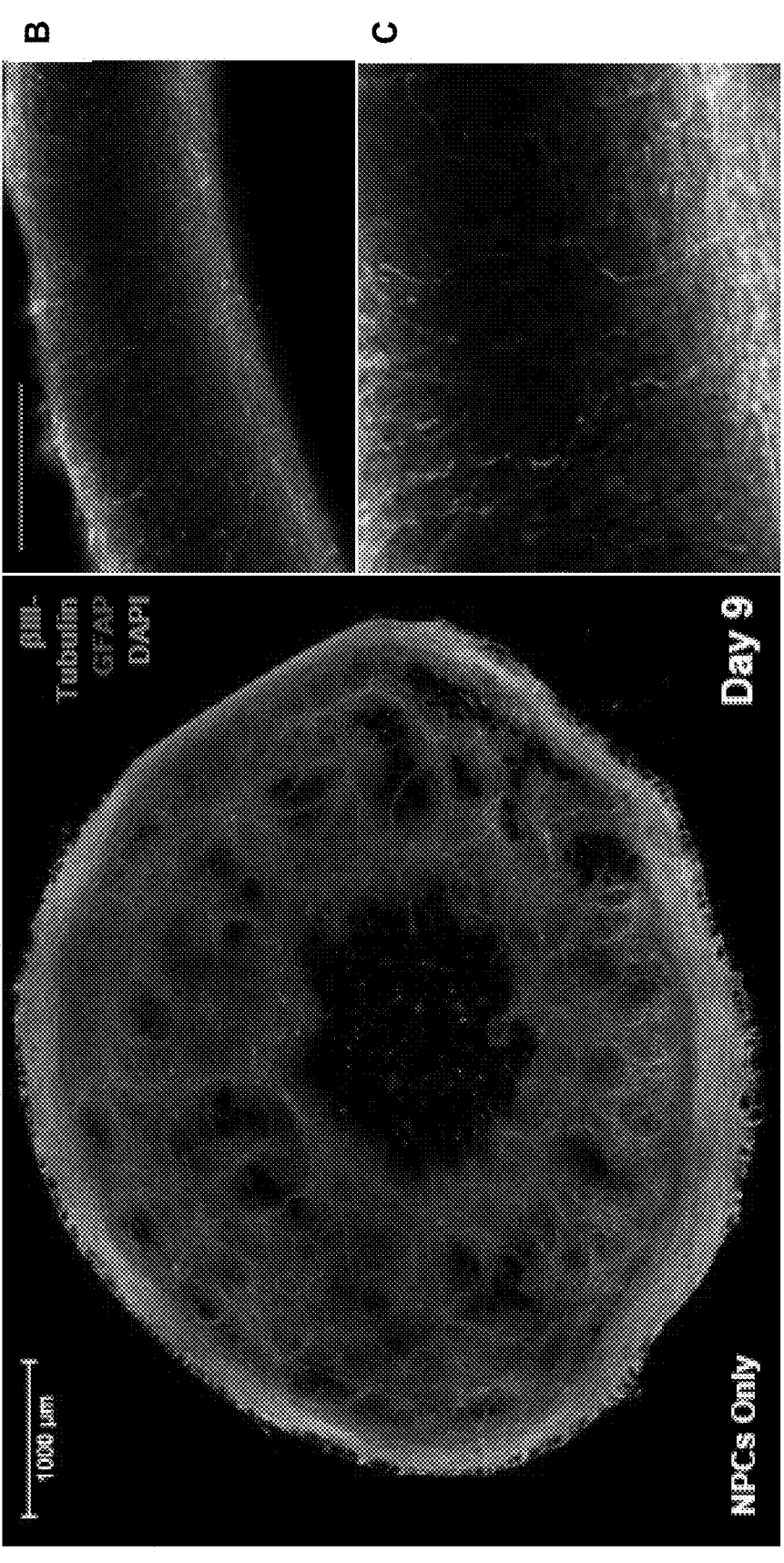

FIGS. 7A-7C demonstrate that neuronal tissue constructs exhibit stratified layers and radial organization of neuronal and glial cells. Maximum projection Z-stacks show immunofluorescence for neuronal (βIII-tubulin, green), glial (GFAP, red), and nuclear (DAPI, blue) markers. (A) Full neuronal construct at day 9 after NPCs were seeded onto an MMP-degradable PEG hydrogel. Endothelial cells and mesenchymal support cells were added for full tissue constructs at day 9 to mimic recruitment by neuroepithelial cells within the neural tube. (B, C) Higher magnification images illustrating stratification and radial orientation of early neuronal and glial populations. Scale bar=250 μm.

FIG. 8 is a table of gene expression data for 3D vascularized neural constructs.

FIG. 9 is a table providing Spearman's correlation data for replicate neuronal constructs formed with or without microglia on days 14 and 21.

Figures 10A, 10B, 10C, 10D, 10E:
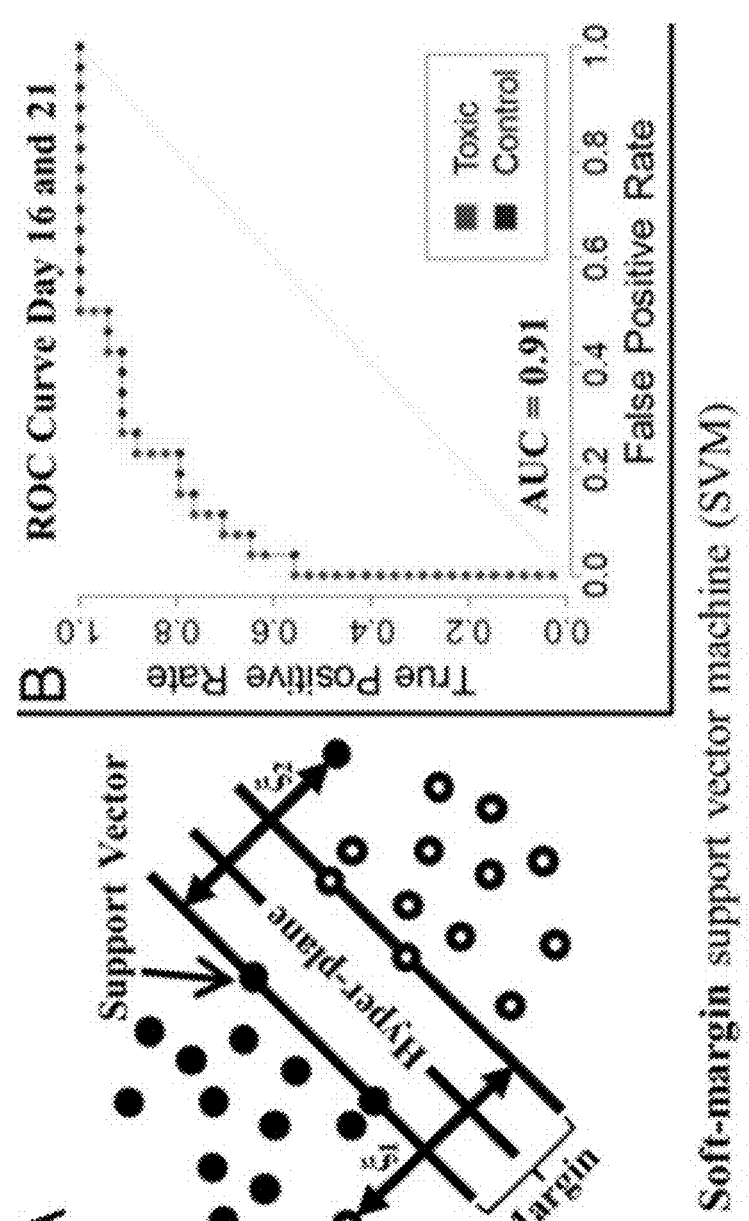

FIGS. 10A-10E present machine learning predictions. (A) A linear support vector machine (SVM) for a 2D problem, where an (n–1)-dimensional hyperplane reduces to a line that separates the classes (filled vs. open circles) and maximizes the closest points between classes (the support vectors, which fix the position and orientation of the hyperplane). The $x_i$s are the examples (points in A), the $y_i$s are their labels (filled or open in A), and w is the weight vector, or vector of coefficients on the features (the dimensions). The linear SVM's output is the weight vector w and the other coefficient b. To make a prediction, the SVM computes the number $w'x_i-b$, and outputs the label 0 (nontoxic, for our application) if this number is less than 0, and 1 otherwise. The extensions required for the soft margin version of the SVM are highlighted in pink in the equation, which minimizes the sum of the distances between incorrectly classified training points (ξi) in addition to the margin, and is used when the data are not linearly separable (Hall M, et al. (2009) The WEKA data mining software: an update. *SIGKDD Explor Newsl.* 11(1):10-18). (B) Performance data (averaged from day 16 (2-day dosing) and day 21 (7-day dosing) are shown in the form of receiver operating characteristic (ROC) curves. The ROC curve plots true positive rate on the y axis against the false positive rate (1—specificity) on the x axis as the threshold is varied. FIGS. 10C-10E present additional receiver operating characteristic (ROC) curve plots and toxins tested (E).

DETAILED DESCRIPTION

Previous in vitro studies have demonstrated the capacity for human pluripotent stem cell-derived neural progenitor cells to self-assemble into layered neuronal tissues that resemble the neocortex (Lancaster el al., *Nature* 501:373 (2013); Kadoshima et al., *Proc. Natl. Acad. Sci. U.S.A.* 110:20284 (2013); Mariani et al., *Proceedings of the National Academy of Sciences* 109:12770 (2012); Eiraku et al., *Cell Stem Cell* 3:519 (2008)), which may be particularly relevant to developmental neurotoxicity screening. However, prior neuronal tissue models lacked critical components of the developing brain such as blood vessels and microglia. The present invention is based at least in part on the Inventors' discovery that human pluripotent stem cell-derived precursor cells cultured in materials that are permissive towards remodeling form highly uniform 3D vascularized neuronal tissues that recapitulate the complexity and organization of human tissues. The Inventors further discovered that the 3D vascularized tissues are useful for screening compounds and, using global gene expression profiles from the tissues, developed a machine learning protocol that correctly classified greater than 90% of test compounds. While it was known that human pluripotent stem cell-derived neuronal tissues provide an alternative to animal testing for modeling human brain development, the Inventors' discovered that it was possible to produce complex human tissue models comprising physiologically relevant human cells and having the high sample uniformity necessary for large-scale, quantitative enhanced throughput screening applications.

Successful strategies to produce in vitro "organoid" models have been reported for a variety of tissues (Ader & Tanaka, *Curr. Opin. Cell Biol.* 31:23 (2014)), but Matrigel and/or suspension culture techniques typically used for these procedures introduce variability that is not well-suited for enhanced throughput quantitative analysis (Singec, *Nat. Methods* 3:801 (2006)). Accordingly, the present invention relates to compositions including three-dimensional tissue constructs and organoids obtained using monolayer culture techniques to assemble precursor cells on chemically-defined bioactive substrates. The present invention also provides methods of using three-dimensional tissue constructs and organoids as highly uniform models of human tissue and for screening potentially toxic agents. Among the advantages offered by the present invention, three-dimensional tissue constructs and organoids of the invention provide biologically-relevant information about the effects of various neurotoxic agents within the complex environment of neural tissue. In addition, the present invention is useful for identifying materials and combinatorial strategies for human tissue engineering.

Compositions

Accordingly, the present invention provides a composition comprising a three-dimensional (3D) tissue construct. As used herein, the term "tissue construct" refers to engineered tissues produced in vitro that comprise complex topologies and geometries (e.g., multi-layered structures, segments, sheets, tubes, sacs). The complex topologies and geometries of the tissue constructs recapitulate cell-to-cell interactions found within native tissues. As used herein, the term "three dimensional (3D) tissue construct" refers to an engineered assemblage of cells and materials that forms a three-dimensional, interconnected complex structure to mimic in vivo physiological conditions. By contrast, two dimensional cultures comprise cells cultivated in a single layer in a tissue culture dish. An engineered tissue construct of the invention comprises at least two layers comprising a homogeneous or heterogeneous population of cells, wherein one layer of the tissue construct is compositionally or architecturally distinct from another layer. In some cases, layers of the tissue construct comprise multiple cell types in spatially-defined positions relative to each other to recapitulate intercellular interactions found within native tissues. In exemplary embodiments, the tissue construct is a 3D neural tissue construct that provides a microenvironment permissive to in vitro development, in three dimensions, to recapitulate neural tissue in vivo. A 3D neural tissue construct of

7

Figures 1A, 1B:
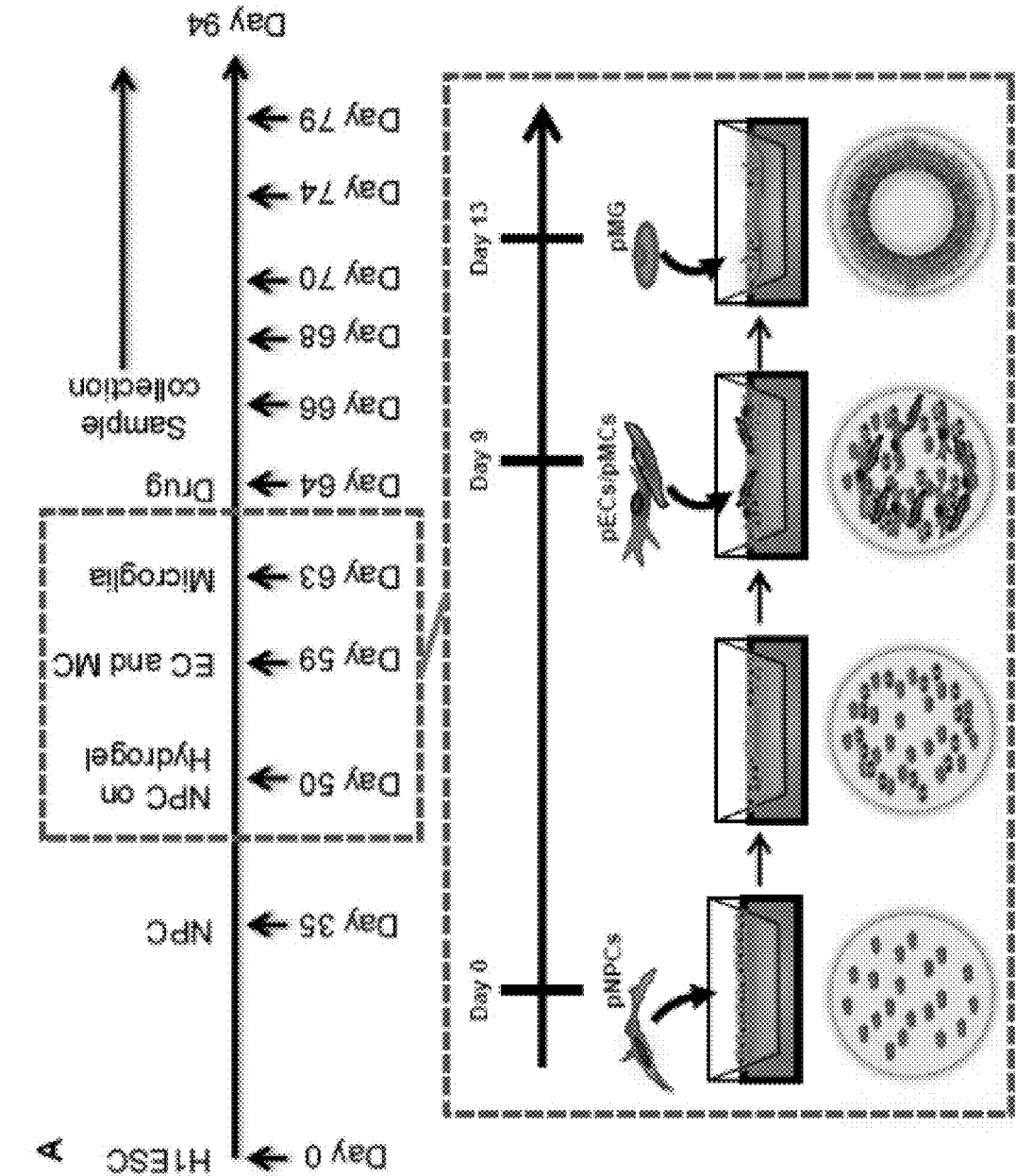
FIGS. 1A-1B present (A) a schematic representation of a strategy for assembling a hydrogel tissue construct. In (A), the upper timeline includes the differentiation protocols for obtaining neural progenitor cells (NPCs) from pluripotent stem cells, while the lower timeline reflects initial formation of tissue construct. Presented in (B) is a schematic representation of the chemistry of hydrogel formation by thiol-ene photopolymerization.

8 the present invention is formed in vitro by the addition of neural progenitor cells to layered tissue comprising neural and glial cell populations. An exemplary embodiment is depicted in FIGS. 1A-1B. According to this embodiment, a vascularized neural tissue construct is obtained by embedding human ES/iPS cell-derived endothelial cells, pericytes, and primitive macrophages (microglial precursors) into a tunable hydrogel displaying specific peptide motifs that promote capillary network formation. To this mesenchymal cell layer, neural and astrocyte precursors are overlayed. The hydrogel is then cultured for about two weeks to form a vascularized neural tissue construct that mimics in vivo cephalic mesenchyme-neural epithelial interactions. Neural progenitor cells (NPCs) and/or components derived from such progenitors are introduced by adding the components to the top of a three-dimensional tissue construct.

In some cases, the 3D neural tissue construct comprises layered neural tissue lacking either vasculature or microglia. In other cases, a 3D neural tissue construct of the invention further comprises vascular and/or microglia components. For example, a 3D neural tissue construct can comprise stratified, vascularized neural epithelium, with or without microglia. Preferably, a 3D vascularized neural tissue construct as described herein has at least one of the following properties: (i) interconnected vasculature; (ii) differentiated cells within the neural tissue construct mutually contact in three dimensions; (iii) having more than one layer of cells; and (iv) demonstrate a function or property characteristic of human neural tissue in vivo or in situ.

In some cases, a composition of the present invention comprises a three-dimensional cortical tissue construct. In such cases, a 3D cortical tissue construct comprises complex tissues that recapitulate the structural organization and vascularization of human cerebral cortex.

Naturally derived ECMs used for three-dimensional culture (e.g., Matrigel® (BD Biosciences, Bedford, MA), collagen gels) are not well-defined, and typically expose cells to a wide variety of signaling factors simultaneously. In order to optimize the influence of a particular type of signal on cell behavior, without interference from numerous other signals acting in concert, alternatives to naturally derived ECMs are preferred. In exemplary embodiments, a 3D tissue construct of the present invention comprises a porous biomaterial such as a hydrogel. The term "hydrogel" refers to a highly hydrated porous material comprising synthetic or biological components formed when an organic polymer (natural or synthetic) is cross-linked via covalent, ionic, or hydrogen bonds to create a 3D open-lattice structure that entraps water molecules to form a gel. Hydrogels appropriate for constructing 3D tissue constructs of the present invention include, without limitation, synthetic hydrogels, bioactive hydrogels, biocompatible hydrogels, cytocompatible hydrogels, chemically defined hydrogels, chemically-defined synthetic hydrogels, and proteolytically degradable hydrogels.

As used herein, "bioactive" is intended to indicate the ability to facilitate a cellular or tissue response, such as differentiation of a pluripotent stem cell, induction of vasculogenesis, neural stem cell differentiation, promotion of cellular attachment, promotion of cell self-assembly, and promotion of cell-cell interactions.

As used herein, the term "biocompatible" refers to the ability of a polymer or hydrogel to perform as a substrate that will support cellular activity, including the facilitation of molecular and mechanical signaling systems, in order to permit proper cell self-assembly or cellular function such as tissue formation, production of soluble bioactive molecules (e.g., growth factors), specific cell behaviors such as migration and proliferation. In some cases, "biocompatibility" means the absence of components having cell- or tissue-damaging effects. As used herein, the term "chemically defined" means that the identity and quantity of each component of a composition (e.g., a hydrogel) is known. An important goal in the fields of pluripotent stem cell culture and directed differentiation of pluripotent stem cells is to develop culture materials and culture media that provide improved performance consistency and reproducibility. In some cases, a chemically defined hydrogel for use in a neural tissue construct provided herein comprises a minimal number of defined components/ingredients.

As used herein, the term "cytocompatible" means the hydrogel material is substantially non-cytotoxic and produces no, or essentially no, cytotoxic degradation products.

As used herein, the term "proteolytically degradable" means that the crosslinked backbone can be cleaved enzymatically or non-enzymatically to break down the scaffold network.

In some embodiments, a hydrogel appropriate for inclusion in a neural tissue construct as described herein is at least partially contained within a three-dimensional structural framework. Preferably, a structural framework comprises a three dimensional structure prepared from one or more polymeric materials, including biopolymers.

A hydrogel appropriate for use in a neural tissue construct of the invention can be prepared using various polymers including, without limitation, poly(ethylene glycol) (PEG), polyvinyl alcohol (PVA), polyvinyl pyrrolidone (PVP), polyacrylamides, and polysaccharides. PEG is a polymer having solubility in water and in many organic solvents and, generally, lacking toxicity, antigenicity, or immunogenicity. PEG can be activated at each terminus to be bifunctional. In other cases, one terminus can be modified to have a reactive moiety. For example, a PEG monomer can be modified to have a relatively inert methoxy moiety (e.g., methoxy-PEG-OH) at one terminus while the other terminus is a hydroxyl group that is readily chemically modifiable. Polysaccharide hydrogels are made by crosslinking natural or semi-synthetic polysaccharides such as alginate, carboxymethylcellulose, hyaluronic acid, and chitosan. The cross-linking reaction allows for the formation of a three-dimensional network made of covalent bonds between the polymer chains—a network that is stable under physiological conditions.

In some embodiments, a hydrogel appropriate for inclusion in a neural tissue construct as described herein is at least partially contained within a three-dimensional structural framework. Preferably, a structural framework comprises a three dimensional structure prepared from one or more polymeric materials, including biopolymers. In other embodiments, it may be useful for the bioactive hydrogel matrix to have additional structure or strength in the absence of a framework or additives. In such cases, a bioactive hydrogel matrix is in a stabilized, crosslinked form.

In exemplary embodiments, hydrogels (e.g., PEG hydrogels, polysaccharide hydrogels) are used to produce 3D tissue constructs of the invention. Cells can be readily encapsulated within these gels using photo-polymerization. See Fairbanks et al., *Adv. Mater.* 21:5005-5010 (2009). Proteins and cells exhibit little to no intrinsic adhesion or interaction with PEG hydrogels. See Drury & Mooney, *Biomaterials* 24(24):4337-51 (2003); Nguyen & West, *Biomaterials* 23(22):4307-14 (2002); and Hoffman, *Adv. Drug Deliv. Rev.* 54(1):3-12 (2002). Thus, PEG provides an ideal "blank slate" upon which one can present specific biological molecules to cells in a controlled manner.

To promote self-assembly of an engineered neural construct that recapitulates vascularized neural epithelium, it is advantageous to use a photo-polymerization strategy that uses "thiol-ene" chemistry. See Fairbanks et al., *Adv. Mater.* 21:5005-5010 (2009). Step-growth thiol-ene photopolymerization is based on a reaction between a thiol and a vinyl group in the presence of a photoinitiator—a reaction that results in a homogeneous, cytocompatible hydrogel. Photopolymerization kinetics can be controlled by altering the concentration of photoinitiator (e.g., radical).

In some cases, a 3D neural tissue construct of the present invention comprises a hydrogel formed using PEG monomers functionalized with norbornene. For example, a 3D neural tissue construct of the present invention can be prepared using a hydrogel comprising a 4-arm or 8-arm PEG monomers reacted with 5-norbornene-2-carboxylic acid to form a norbornene-functionalized PEG solution.

In some cases, a hydrogel appropriate for neural tissue constructs described herein comprise a bioactive agent such as a growth factor, a cytokine, a bioactive polypeptide or peptide (e.g., RGD-containing peptides), or any other bioactive ligand capable of interacting with a biomolecule of the cells cultured on or within the hydrogel. Peptides comprising the fibronectin-derived RGD peptide sequence include, without limitation, RGDS (SEQ ID NO:7), CRGDS (SEQ ID NO:2), Ac-CRGDS (SEQ ID NO:11); CRGDS-CONH(2) (SEQ ID NO:12), Ac-CRGDS-CONH(2) (SEQ ID NO:13), RGDSC (SEQ ID NO:8), CCRGDS (SEQ ID NO:9), and CCCRGD (SEQ ID NO:10). The number and type of appropriate bioactive agents for the present invention will depend on the types of cells cultured on the hydrogel. Examples of suitable bioactive ligands include, without limitation, carboxyl, amine, phenol, guanidine, thiol, indole, imidazole, hydroxyl, sulfate, norbornene, maleimide, laminin, fibronectin, fibrinogen, peptide sequences, or combinations thereof. Bioactive ligands can be covalently incorporated into PEG hydrogels using a thiol-ene-based photopolymerization strategy.

Other PEG formulations may be useful for methods of using the tissue constructs in, for example, screening applications (i.e., for an agent having a certain activity or effect on a cell type within the construct). In some cases, PEG formulations comprising non-degradable crosslinkers are used to obtain neural construct described herein. In other cases, a hydrogel formed using PEG monomers and comprising various concentrations of extracellular matrix-derived peptides or other peptides (e.g., peptides comprising the integrin-binding sequence CRGDS (SEQ ID NO:2)) can be used. For example, dextran hydrogels suitable for tissue engineering have been produced by introducing primary amine groups for covalent immobilization of extracellular-matrix-derived peptides (Levesque and Shoichet, *Biomaterials* 27(30):5277-85 (2006)). In yet other cases, hydrogels comprise different crosslinking densities (i.e., altering stiffness of the hydrogel) or, in some cases, a MMP-degradable crosslinker.

A 3D neural tissue construct of the present invention can be prepared by dispersing isolated cells or an isolated cell population within or on a hydrogel. As used herein, an "isolated cell" is a cell that has been substantially separated or purified away from other cell types or biological substances. As used herein, the term "population" refers to a collection of cells, such as a collection of progenitor and/or differentiated cells. As used herein, the term "differentiated" as it relates to the cells of the present invention can refer to cells that have developed to a point where they are programmed to develop into a specific type of cell and/or lineage of cells. Similarly, "non-differentiated" or "undifferentiated" as it relates to the cells of the present invention can refer to progenitor cells, i.e., cells having the capacity to develop into various types of cells within a specified lineage. In exemplary embodiments, a 3D neural tissue construct of the invention is produced by dispersing one or more defined progenitor cell populations (e.g., one or more isolated populations of neural progenitor cells). Preferably, as an initial step, a hydrogel is seeded by dispersing neural progenitor cells within or on a hydrogel. In some cases, the neural progenitor cells are derived from human pluripotent stem cells including, for example, human induced pluripotent stem cells. A hydrogel comprising dispersed neural progenitor cells is then cultured under conditions and for a length of time sufficient to promote differentiation of human neural progenitor cells dispersed therein. The hydrogel so cultured can be further seeded by dispersing within or on the cultured hydrogel one or more additional human cell types. Preferably, the hydrogel following dispersal of one or more additional human cell types comprises cell populations such as, for example, pericytes, microvascular endothelial cells, glial cells (e.g., astrocytes and oligodendrocytes), neuronal cells (e.g., GABAergic and glutamatergic neurons), stromal cells, Schwann cells, undifferentiated cells (e.g., embryonic cells, stem cells, and progenitor cells), endoderm-derived cells, mesoderm-derived cells, ectoderm-derived cells, and cancer-derived cells or combinations thereof including, without limitation, human endothelial cells, human mesenchymal cells, human primitive macrophages, and human pericytes. The hydrogel comprising such dispersed human cells can be cultured under culture conditions that promote cell differentiation for a length of time sufficient to be able to observe formation of a 3D vascularized neural tissue construct comprising human neurons and glial cells. Upon differentiation of neural progenitor cells and the addition of cell types such as endothelial cells, human mesenchymal cells, human primitive macrophages, and human pericytes, the resulting three-dimensional neural tissue construct represents one or more stages of human brain development.

In some cases, a hydrogel is further seeded by dispersing within or on the hydrogel one or more bioactive agent that modulates a function or characteristic of a cell. Such a bioactive agent can be dispersed within or on the hydrogel prior to or following dispersal of a cell type described herein.

Advantageously, 3D neural tissue constructs of the invention provide physiologically relevant in vitro models of the developing human brain including vascular networks having characteristics of the blood brain barrier and microglia derived from differentiation of primitive macrophages. In exemplary embodiments, a 3D tissue construct of the invention comprises elements important for or involved in development of the mammalian (e.g., human, non-human primate) brain including, without limitation, neural progenitor cells, endothelial cells (e.g., human microvascular endothelial cells), mesenchymal cells, and primitive macrophages. Neural progenitor cells that differentiate within the construct provide neuronal and glial populations. Endothelial cells and mesenchymal cells contribute to an interconnected vasculature, and primitive macrophages differentiate to populate the construct with microglia. In some cases, cells populating a tissue construct of the invention are derived from human pluripotent stem cells, such as human embryonic stem cells (hESCs) or human induced pluripotent stem cells (iPSCs), under chemically defined, xenogeneic material-free conditions. In exemplary embodiments, human pluripotent stem cells are differentiated in vitro under chemically defined, xenogeneic material-free conditions to separately derive distinct tissue construct components as described in U.S. application Ser. No. 14/986,382, and U.S. application Ser. No. 14/986,224, respectively. Such cells can self-assemble into a neural tissue construct that lacks vasculature or microglia, or that is subsequently seeded with vascular cells or microglia. In other cases, it is possible to enhance differentiation within a 3D neural tissue construct by adding cells that are at intermediate stages such as earlier neural progenitor cells.

In exemplary embodiments, 3D neural tissue construct is produced by culturing neural progenitor cells (e.g., human pluripotent stem cell-derived neural progenitor cells) on a bioactive synthetic hydrogel (e.g., PEG hydrogel) to promote differentiation and self-assembly of neuronal and glial populations. Such neural progenitor cells can be seeded on a hydrogel at a density between about 10,000 cells/well to about 500,000 cells/well (e.g., about 10,000 cells/well; 20,000 cells/well; 30,000 cells/well; 40,000 cells/well; 50,000 cells/well; 75,000 cells/well; 100,000 cells/well; 150,000 cells/well; 200,000 cells/well; 250,000 cells/well; 300,000 cells/well; 400,000 cells/well; 450,000 cells/well; 500,000 cells/well). Preferably, neural progenitor cells are seeded at a density between about 50,000 to about 200,000 cells/well.

Subsequently, vascular cells and microglia precursors (primitive macrophages) are added to the hydrogel construct. The addition of vascular cells and primitive macrophages mimics recruitment of blood vessels and microglia after formation of the neural tube. When cultured on bioactive synthetic hydrogels, the precursors will self-assemble to form complex multilayered, highly uniform neuronal tissue-like constructs having similar gross morphological features between samples. Vascular cells and/or primitive macrophages can be seeded on a hydrogel at a density between about 10,000 cells/well to about 500,000 cells/well (e.g., about 10,000 cells/well; 20,000 cells/well; 30,000 cells/well; 40,000 cells/well; 50,000 cells/well; 75,000 cells/well; 100,000 cells/well; 150,000 cells/well; 200,000 cells/well; 250,000 cells/well; 300,000 cells/well; 400,000 cells/well; 450,000 cells/well; 500,000 cells/well). Preferably, vascular cells and/or primitive macrophages are seeded at a density between about 50,000 to about 200,000 cells/well.

In exemplary embodiments, a 3D tissue construct is seeded with progenitors of the myeloid lineages (i.e., granulocyte, macrophage, erythroid, and megakaryocyte) from pluripotent stem cell-derived hematovascular mesoderm. In humans, common myeloid progenitors (CMPs), which are progenitor cells committed to the myeloid lineages, express CD34 and IL-3R alpha (CD123). Progenitors of the myeloid lineages (i.e., granulocyte, macrophage, erythroid, and megakaryocyte) can be seeded on a hydrogel at a density between about 10,000 cells/well to about 500,000 cells/well (e.g., about 10,000 cells/well; 20,000 cells/well; 30,000 cells/well; 40,000 cells/well; 50,000 cells/well; 75,000 cells/well; 100,000 cells/well; 150,000 cells/well; 200,000 cells/well; 250,000 cells/well; 300,000 cells/well; 400,000 cells/well; 450,000 cells/well; 500,000 cells/well). Preferably, progenitors of the myeloid lineages (i.e., granulocyte, macrophage, erythroid, and megakaryocyte) are seeded at a density between about 50,000 to about 200,000 cells/well.

Human hematovascular mesodermal cells can be obtained according to a method that comprises culturing human pluripotent stem cells for about two days in the presence of a serum-free, albumin-free, chemically-defined culture medium as provided herein that is supplemented to further comprise one or more of the following: a Rho kinase inhibitor (ROCK inhibitor) (e.g., Y-27632), bone morphogenetic protein 4 (BMP4), Activin A, and lithium chloride (LiCl). In some cases, the human pluripotent stem cells are cultured under hypoxic (i.e., oxygen level lower than atmospheric) conditions. In exemplary embodiments, the cells are cultured as described herein in the presence of 5% $O_2$. Methods can further comprise obtaining myeloid progenitors by expanding such pluripotent stem cell-derived hematovascular mesodermal cells under normoxic (i.e., atmospheric oxygen levels, about 20% $O_2$) conditions in a chemically defined, xeno-free culture medium comprising or consisting essentially of FGF2, VEGF, TPO, SCF, IL-6, and IL-3. The method can comprise the further step of culturing such cells under normoxic conditions in a myeloid differentiation culture medium. In exemplary embodiments, a myeloid differentiation culture medium is a chemically defined, xeno-free medium comprising granulocyte macrophage colony-stimulating factor (GM-CSF), which is also known as colony stimulating factor 2 (CSF2) and is a cytokine produced mainly by macrophages and activated T cells. Recombinant human GM-CSF and related products are commercially available.

Neural tissue constructs described herein can be modified to have different configurations or morphologies by seeding a construct with a larger or smaller population of neural progenitor cells and, consequently, altering the number, size, and composition (e.g., identity) of neuron and/or glial cell populations. Likewise, any cellular components or materials used to obtain a neural tissue construct as described herein can be modified or optimized to, for example, tailor a screening method or other use of a neural tissue construct provided herein, to assay developmental aspects of human neural tissue (e.g., modify culture/growth periods, incorporate additional cell types, remove certain neural tissue construct components), or to vary material properties of a neural tissue construct (e.g., vary adhesion ligand, crosslinking agent, etc.).

Although human cells are preferred for use in the invention, the cells to be used in tissue constructs of the invention are not limited to cells from human sources. Cells from other mammalian species including, but not limited to, equine, canine, porcine, bovine, feline, caprine, murine, and ovine sources can be used. Cell donors may vary in development and age. Cells can be derived from donor tissues of embryos, neonates, or older individuals including adults.

In some cases, a tissue construct of the present invention may comprise recombinant or genetically-modified cells in place of or in addition to unmodified or wild-type ("normal") cells. For example, it can be advantageous in some cases to include recombinant and genetically-modified cells that produce recombinant cell products, growth factors, hormones, peptides or proteins for a continuous amount of time or as needed when biologically, chemically, or thermally signaled due to the conditions present in culture. Procedures for obtaining recombinant or genetically modified cells are generally known in the art, and are described in Sambrook el al, *Molecular Cloning, A Laboratory Manual*, Cold Spring Harbor Press, Cold Spring Harbor, N.Y. (1989), incorporated herein by reference.

In another aspect, the present invention provides 3D tissue constructs comprising one or more cell types derived from a particular mammalian subject (e.g., a particular human subject). In some cases, one or more cell types derived exhibit one or more specific phenotypes associated with or resulting from a particular disease or disorder of the particular mammalian subject. Subject-specific cells can be obtained or isolated from a target tissue of interest by biopsy or other tissue sampling methods. In some cases, subject-specific cells are manipulated in vitro prior to use in a tissue construct of the invention. For example, subject-specific cells can be expanded, differentiated, genetically modified, contacted to polypeptides, nucleic acids, or other factors, cryo-preserved, or otherwise modified prior to use in a tissue construct of the present invention. In some cases, subject-specific cells are differentiated prior to, during, or after encapsulation in a three-dimensional tissue construct of the invention. In other cases, subject-specific cells for use in a tissue construct of the invention are induced pluripotent stem cells obtained by reprogramming somatic cells of the subject according to methods known in the art. See, for example, Yu et al., *Science* 324(5928):797-801 (2009); Chen et al., *Nat Methods* 8(5):424-9 (2011); Ebert et al., *Nature* 457(7227):277-80 (2009); Howden et al., *Proc Natl Acad Sci USA* 108(16):6537-42 (2011). Human induced pluripotent stem cells allow modeling of drug responses in a genetically diverse population of individuals, including those individuals with genetic diseases. Even the safest drugs may cause adverse reactions in certain individuals with a specific genetic background or environmental history. Accordingly, 3D tissue constructs comprising cells derived from iPS cells obtained from individuals having known susceptibilities or resistances to various drugs or diseases will be useful in identifying genetic factors and epigenetic influences that contribute to variable drug responses.

In exemplary embodiments, human pluripotent stem cells (e.g., human ESCs or iPS cells) are cultured in the absence of a feeder layer (e.g., a fibroblast layer) and in the presence of a chemically defined, xenogen-free substrate. For example, human pluripotent cells can be cultured in the presence of a substrate comprising vitronectin, a vitronectin fragment or variant, a vitronectin peptide, a self-coating substrate such as Synthemax® (Corning), or combinations thereof. In exemplary embodiments, the chemically-defined, xeno-free substrate is a plate coated in vitronectin peptides or polypeptides (e.g., recombinant human vitronectin).

In another aspect, the present invention provides an organoid culture system. As used herein, the term "organoid" refers to a tissue-like structure (i.e., exhibiting structural properties of a particular tissue type) that resembles a whole organ and is assembled in vitro by the separate addition and self-organization of various cell types including, but not limited to, pluripotent stem cells, fetal neural stem cells, and isolated organ progenitors. See, e.g., Lancaster and Knoblich, *Science* 345(6194) (2014). In exemplary embodiments of the invention, an organoid culture system comprises a three-dimensional construct comprising hydrogel-encapsulated cells and provides a physiologically relevant microenvironment for analysis or perturbation of cell-cell interactions, cell-matrix interactions, and morphogenesis in three-dimensional culture. In some cases, an organoid culture system provides a microenvironment that at least partially recapitulates tubulogenesis (e.g., capillary tubulogenesis) and vasculogenesis including, for example, the formation of polarized epithelia with lumens surrounded by capillary-like structures having endothelial features. In exemplary embodiments, capillary tubulogenesis in a 3D tissue construct of the invention recapitulates principles of both angiogenesis, postnatal vasculogenesis, and other developmental steps that closely resemble embryonic neo-vascularization. Montano et al., *Tissue Engineering Part A* 16(1):269-82 (2010); Kusuma et al., *Proceedings of the National Academy of Sciences* 110:12601-12606 (2013).

In some cases, a 3D tissue construct of the present invention further comprises isolated biological components. As used herein, an "isolated" biological component (such as a protein or organelle) has been substantially separated or purified away from other biological components in the cell of the organism in which the component naturally occurs, such as other chromosomal and extra-chromosomal DNA and RNA, proteins, and organdies. As used herein, the term "isolated protein" includes proteins purified by standard purification methods. The term also embraces proteins prepared by recombinant expression in a host cell, as well as chemically synthesized proteins, or fragments thereof.

Engineered three-dimensional tissue constructs of the present invention can be prepared, grown, and maintained in any suitable tissue culture vessel that permits production, growth, and maintenance of the constructs. Suitable vessels include Transwell™ permeable support devices and T-75 flasks. In some cases, a 3D tissue construct of the invention is prepared and/or maintained in a multi-well tissue culture vessel. A multi-well vessel is advantageous to facilitate mechanization and large-scale or high-throughput screening of neural construct according to methods of the invention. For example, a 3D tissue construct of the present invention can be prepared or provided using a multi-well tissue culture vessel that facilitates high-throughput assessment of, for example, cellular interactions, in vitro development, toxicity, and cell proliferation upon contacting a chemical compound of interest to the neural construct. In some cases, a tissue culture vessel may be coated with polypeptides or peptides that promote cell proliferation and/or differentiation (e.g., vitronectin, fibronectin) and placed in an incubator at 37° C. prior to seeding with cells.

Any appropriate method or methods can be used to confirm uniformity and the presence or absence of certain components in a 3D tissue construct provided herein. Suitable methods for detecting the presence or absence of biological markers are well known in the art and include, without limitation, immunohistochemistry, qRT-PCR, RNA sequencing, and the like for evaluating gene expression at the RNA level. In some cases, methods such as immunohistochemistry are used to detect and identify cell types or biomolecules within a 3D tissue construct. For example, whole tissue constructs or portions thereof can be stained for specific differentiation markers by immunohistochemistry. In some cases, it will be advantageous to perform dual-label immunofluorescence to assess the relative expression of individual marker proteins or to detect multiple progenitor or differentiated cell types within a construct. Appropriate primary and secondary antibodies are known and available to those practicing in the art. In addition, microarray technology or nucleic acid sequencing (e.g., RNA sequencing) can be used to obtain gene expression profiles for 3D engineered tissue compositions of the invention. Myeloid markers and macrophage associated markers include, for example, CD14, CD16, CSFR-1, CD11b, CD206 (also known as macrophage mannose receptor or MMR), CD68, and CD163. Quantitative methods for evaluating expression of markers at the protein level in cell populations are also known in the art. For example, flow cytometry is used to determine the fraction of cells in a given cell population that express or do not express biological markers of interest. Biological markers for perivascular cells and microglia include antibodies having specificity to CD45, CD68, or HLA-DR complex.

Differentiation potential of progenitor cells encapsulated in a 3D tissue construct of the invention can be examined for changes in phenotype, organization, and the presence of certain proteins using, for example, magnetic sorting, flow cytometry, immunofluorescence, bright-field microscopy, and electron microscopy. In some cases, it will be advantageous to fix or freeze tissue constructs of the invention for histology or microscopy. For example, 3D tissue constructs of the invention can be fixed in formalin or paraformaldehyde for plastic embedment and sectioning using routine methods. Scanning electron microscopy (SEM) is useful to detect and analyze the formation of tubular structures in tissue constructs of the invention. In particular, SEM can be used to study cross-sectioned tissue constructs to detect blood vessel formation (e.g., large vessels, small capillaries). In exemplary embodiments, confocal microscopy can reveal the distribution of cell types and vascular structures throughout a three-dimensional tissue construct of the invention. In some cases, a three-dimensional assembly of images obtained by confocal microscopy is used to analyze the distribution and organization of various cells and structures.

Morphology also can be used to characterize culture components, but cells of different origins may share similar features and be difficult to distinguish using morphology alone. Where appropriate, excitatory and inhibitory synaptic potentials can be analyzed using, for example, extra- or intracellular recording techniques.

TABLE 1

Biological Markers of Differentiated Cell Types in Vascularized Neural Tissue Constructs

| Cell Type | Marker | Target Cell |
|---|---|---|
| Epithelial | Tight junction protein (TJP1); also known as Zona occludens protein 1 (ZO-1) | Epithelial tight junctions |
| | Keratin | Epithelial (general) |
| | Collagen IV | Epithelial basement membrane |
| Mesenchymal | α-SMA (alpha smooth muscle actin) | Pericytes |
| | Vimentin | Pericytes |
| | PDGFR-β (platelet derived growth factor receptor beta) | Pericytes |
| Endothelial | PECAM-1 (Platelet-Endothelial Cell Adhesion Molecule-1; also known as CD-31) | endothelial cells; blood vessels |
| Neuronal | N-CAM (neural cell adhesion molecule) | Neurons (including postmigratory immature neurons) |
| | A2B5 | Glial progenitors; oligodendrocyte and astrocyte progenitors |

Methods of the Invention

In another aspect, the present invention provides methods for producing and using heterogeneous engineered tissue constructs that mimic structural elements important for or involved in development of the mammalian brain. In particular, provided herein are methods of using 3D tissue constructs for high throughput screening of candidate compounds and identifying agents that are toxic to or hinder the development of one or more components of the tissue construct. The present invention also provides methods for screening 3D tissue constructs candidate therapeutic drugs, modeling a disease or pathological disorder, assaying 3D tissue constructs for viability and proliferative capacity of cells of the construct under various culture conditions, and methods using neural organoid tissues for compounds exhibiting developmental neurotoxicity. As described herein, the methods of the present invention are advantageous over standard in vitro and in vivo methodologies for toxigenicity testing (e.g., in vivo mouse bioassays for toxigenicity testing). In particular, the methods described herein provide sensitive, reproducible, and quantifiable methods for neurotoxin screening. The methods are better alternatives to in vivo mouse bioassays (MBA), an assay which is quantifiable assay but error-prone. In addition, MBA requires a large number of animals and is not easily standardized between laboratories or scalable for high-throughput screening. Shortcomings of the MBA and other animal-based assays have incited a push from regulatory agencies, including the Food and Drug Administration (FDA) and the United States Department of Agriculture, to develop cell-based models comprising more physiologically relevant human cells and having the sensitivity and uniformity necessary for large-scale, quantitative in vitro modeling and screening applications (National Institutes of Health, 2008).

In exemplary embodiments of methods of the present invention, a 3D neural tissue construct provided herein is used to screen test compounds for known and unknown toxicities. For example, a 3D neural tissue construct can be contacted to a test compound and assayed for any effect on any of the cell types contained therein (e.g., neuron, glial cell, vascular cell, microglia, other differentiated cell subtypes). In exemplary embodiments, screening methods comprise contacting one or more test compounds to a 3D tissue construct of the present invention and detecting a positive or negative change in a biological property or activity such as, without limitation, gene expression, protein expression, cell viability, and cell proliferation. The manner in which a test compound has an effect on a particular biological activity of the constructs of the present invention will depend on the nature of the test compound, the composition of the tissue construct and the particular biological activity being assayed. However, methods of the present invention will generally include the steps of (a) culturing a 3D tissue construct as provided herein with a test compound, (b) assaying a selected biological activity of the artificial tissue construct, and (c) comparing values determined in the assay to the values of the same assay performed using a 3D tissue construct having the same composition as the construct contacted by the test compound but cultured in the absence of the test compound (or in the presence of a control). Detecting a positive or negative change in a biological property or activity of a cell of the tissue construct can comprise detecting at least one effect of a test compound on morphology or life span of a cell or tissue within the contacted tissue construct, whereby a test compound that reduces the life span of the cells or tissues or has a negative impact on the morphology of the cells or tissues is identified as toxic to human neural tissue. In some cases, detecting comprises performing a method such as RNA sequencing, gene expression profiling, transcriptome analysis, metabolome analysis, detecting reporter or sensor, protein expression profiling, Forster resonance energy transfer (FRET), metabolic profiling, and microdialysis. Test compounds can be screened for effects on gene expression in the contacted tissue construct, where differential gene expression as compared to an uncontacted tissue construct is detected.

In exemplary embodiments, detecting and/or measuring a positive or negative change in a level of expression of at least one gene following exposure (e.g., contacting) of a 3D neural construct to a test compound comprises whole transcriptome analysis using, for example, RNA sequencing. In such cases, gene expression is calculated using, for example, data processing software programs such as Light Cycle, RSEM (RNA-seq by Expectation-Maximization), Excel, and Prism. See Stewart et al., *PLoS Comput. Biol.* 9:e1002936 (2013). Where appropriate, statistical comparisons can be made using ANOVA analyses, analysis of variance with Bonferroni correction, or two-tailed Student's I-test, where values are determined to be significant at $P<0.05$. Any appropriate method can be used to isolate RNA or protein from neural constructs. For example, total RNA can be isolated and reverse transcribed to obtain cDNA for sequencing.

Test compounds that are suitable for screening according to the methods provided herein include any for which one wishes to determine the effect the compound has on development of the brain of a mammal. It will be readily apparent to the skilled artisan that the test compounds will include those compounds which are suspected of having one or more deleterious effects on cell or tissue of a 3D construct of the invention. Ideally, test compounds cover a range of potential cell toxicities including, without limitation, heavy metals (e.g., lead, cadmium) and kinase inhibitors (e.g., MEK inhibitor). Test compounds can include FDA-approved and non-FDA-approved drugs (including those that failed in late stage animal testing or in human clinical trials) having known or unknown toxicity profiles. Test compounds can include those included in the NIH clinical collection. Some of the toxins, such as MEK inhibitors may affect all or most cell types of a 3D tissue construct.

Any of the cell types can be targeted, including vasculature, microglia, neurons, glial cells, and any interactions between them. Blood brain barrier junction properties are another example, although we did not strictly prove we have "blood brain barrier" function (many of the appropriate attachments and genes were expressed, though).

Test compounds can be dissolved in a solvent such as, for example, dimethyl sulfoxide (DMSO) prior to contacting to an engineered tissue construct provided herein. In some cases, identifying agents comprises analyzing the contacted 3D tissue construct for positive or negative changes in biological activities including, without limitation, gene expression, protein expression, cell viability, and cell proliferation. For example, microarray methods can be used to analyze gene expression profiles of a 3D tissue construct prior to, during, or following contacting the plurality of test compounds to the construct. Gene expression profiles can be obtained for multiple time points and/or multiple 3D tissue constructs. In some cases, gene expression profiles do not directly reflect temporal changes during the initial formation of vascular networks in sECM but, instead, identify genes robustly expressed at each time point. In some cases, a method of the present invention further comprises additional analyses such as metabolic assays and protein expression profiling.

In yet another aspect, the present invention provides methods for evaluating known and potential environmental teratogens. As used herein, the term "teratogen" refers to any environmental factor that can produce a permanent abnormality in structure or function, restriction of growth, or death of an embryo or fetus. A method of the invention can comprise contacting candidate teratogens to a 3D neural tissue construct described herein and screening for developmental abnormalities in the construct. Development abnormalities can include, without limitation, vascular malformations, other defects of vascular origin, neoplasias.

In another aspect, the present invention provides methods for in vitro modeling of vascular dysmorphogenesis. In particular, the present invention provides a method in which candidate agents are screened for antiangiogenic, neurotoxic, and/or teratogenic effects using a 3D neural construct as provided herein. More particularly, the methods comprise screening for neurotoxic effects (e.g., inhibition of neuronal growth) and/or detrimental effects on endothelial cells or blood vessel formation (e.g., vascular dysmorphogenesis, angiogenic outgrowth, or blood vessel remodeling) upon exposure to known and unknown agents. Changes in cell viability and proliferative capacity can be detected using, for example, cell stains and $^3$H-thymidine incorporation.

In another aspect, the present invention provides methods for in vitro modeling of neurodegeneration using organoid constructs. In particular, the invention provides an organoid for studying biological phenomena associated with neurodegeneration and for detecting or measuring the expression of genes and proteins associated with neurodegenerative disorders such as Parkinson's disease. In addition, the organoid construct model is useful for screening novel drugs and growth factors and may reduce the need for invasive animal experiments. A method can comprise contacting a neural construct described herein to one or more candidate agents and screening for biological processes associated with neurodegenerative phenotypes including, without limitation, demyelination, axonal damage, protein aggregation, and neurite loss.

It may be advantageous in some cases to employ a machine learning approach for methods that include, for example, associating characteristic profiles with various cell types and/or with developmental neurotoxicity. For example, in some cases, one or more machine learning algorithms are employed in connection with a method of the invention to analyze data detected and obtained by RNA sequencing or gene expression profiling of 3D neural constructs prior to, during, or following exposure of the constructs to known agents having developmental neurotoxicity. In addition, one or more machine learning algorithms can be used to identify gene sets that predict the neural toxicity of chemicals even in the absence of pre-existing toxicity information. Generally, machine learning algorithms are used to construct models that accurately assign class labels to examples based on the input features that describe the example. In some cases, machine learning algorithms apply a simple linear separator or a (possibly weighted) vote of individual features, or distance-based methods. See FIGS. 5A-5D and related discussion in the Examples section below.

In some cases, a linear support vector machine (SVM) is used to construct a predictive model of developmental neurotoxicity. Generally, SVMs belong to the family of generalized linear models and are useful to construct a predictive model for a variable of interest ("the class") using other variables and training data in which the values of variables including the class are known. A linear SVM is essentially an $(n-1)$-dimensional hyper-plane that separates the instances of two classes in the n-dimensional feature space. Linear SVMs exhibit good classification performance on gene expression data. With respect to the present invention, a SVM can perform the following task specification:

Given: RNA-seq gene expression measurements for roughly 19K genes on one day or on several different days following exposure to various drugs, together with a neural toxicity label on each drug.

Do: Construct a model that, from the same type of expression data on a new drug, can accurately identify if the drug is neural toxic.

A linear SVM's output is the weight vector w and the other coefficient b. These are loosely analogous to the coefficients in other linear models such as logistic regression, although they are used somewhat differently to make predictions on new data points. To make a prediction, the SVM outputs the number $w^t x_i - b$, and outputs the label 0 (non-toxic) if this number is less than 0, and 1 otherwise. While the numerical output does not have a probabilistic interpretation as does the output of logistic regression, a logistic regression model can be built with one input variable—the SVM's output—from the same training set to output a probability of "toxic."

In exemplary embodiments, the ability of a SVM to predict the developmental neural toxicities of other compounds is estimated. In some cases, an unbiased method that provides relatively high variance is used. In other cases, a nearly unbiased (i.e., slightly pessimistic) method that provides lower variance is used. These methods are standards in supervised machine learning and statistical classification. An unbiased method comprises collecting a set of new compounds (not included in the training set) but whose neural toxicities are known; generating RNA-Seq data for these compounds; and testing the predictive model on them after the model has been constructed. This is considered to be blinded trial because researchers running the SVM do not know which compounds are included or what fraction of the compounds are toxic. This information is revealed only after the SVM's predictions are made.

In some cases, a lower-variance evaluation method, such as leave-one-out cross-validation, is employed. Where there are N data points (compounds) in a training set, the method proceeds in N steps. In each step, a different data point is held out of the training set and the SVM is trained on the remaining data points. A prediction is made on the held-aside data point. Hence every data point is a test case exactly once, for a model trained without that data point. Results are aggregated over all the folds, or test cases, to estimate how well the SVM model trained on all the data will perform on a new data point (compound). The method has lower variance because it tests on more compounds—all the compounds of the training set—but is slightly pessimistic because each training set is slightly smaller (one less) than the actual training set.

Using the above leave-one-out cross-validation methodology, numbers of true positive (toxic) predictions (TP), as well as false positive (FP), true negative (non-toxic, TN), and false negative predictions (FN) are computed. Using these numbers, accuracy (i.e., fraction of predictions that are correct) can be computed. In addition, one can compute sensitivity, or true positive rate, or recall [TP/(TP+FN)]; specificity [TN/(TN+FP)]; and precision, or positive predictive value [TP/(TP+FP)]; and other metrics such as F-measure and negative predictive value. Nevertheless, all of these metrics depend on not only the model that produces probabilistic predictions for toxicity but also the probability threshold at which we make positive predictions, such as 0.5. Hence it is common in machine learning and statistical classification to report "thresholdless" curves and or metrics, the most popular being the receiver operating characteristic (ROC) curve and the area under this curve (AUC). The ROC curve plots true positive rate on the y-axis against the false positive rate (1—specificity) on the x-axis as the threshold is varied. Random uniform guessing produces a diagonal from lower left to upper right corner and AUC of 0.5, while perfect prediction produces a graph that goes up to the upper left corner and then across and AUC of 1.0.

In a further aspect, provided herein is a tissue construct screening system. A tissue construct screening system can comprise an analytical device configured to obtain data comprising measurements from a 3D human vascularized neural tissue construct provided herein. The system can further comprise a computer controller configured to receive the data from the analytical device; and a machine-based adaptive learning system trained using known gene expression data and configured to select a subset of features from the data using a feature selection algorithm. The subset of features corresponds to a change in a level of expression of at least one gene following exposure to a known or unknown test compound. In some cases, the measurements comprise gene expression data obtained from microarrays.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

As used herein, "a medium consisting essentially of" means a medium that contains the specified ingredients and those that do not materially affect its basic characteristics.

As used herein, "serum-free" means that a medium does not contain serum or serum replacement, or that it contains essentially no serum or serum replacement. For example, an essentially serum-free medium can contain less than about 1%, 0.9%, 0.8%, 0.7%, 0.6%, 0.5%, 0.4%, 0.3%, 0.2% or 0.1% serum.

As used herein, "effective amount" means an amount of an agent sufficient to evoke a specified cellular effect according to the present invention.

As used herein, "about" means within 5% of a stated concentration range, density, temperature, or time frame.

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

Example 1—Producing Vascularized Neuronal Tissue Constructs

Hydrogel polymerization: Thiol-ene photo-polymerization provides mix and match adaptability for customizing hydrogels, since any peptide that includes cysteine in the amino acid sequence can be coupled into a hydrogel. Polyethylene glycol (PEG) hydrogels were formed using thiol-ene photopolymerization chemistry, with modifications from previously a published protocol (Fairbanks et al., *Adv Mater* 21(48):5005-5010 (2009)). Stock solutions of 8-arm PEG-norbornene (20000 MW, JenKem USA, 8ARM (TP)-NB-20K) were prepared at a final concentration of 300 mg/mL by dissolving 300 mg of solid/0.8 mL PBS to account for volume occupied by 8-arm PEG-norbornene solid, sterile filtered through a 0.2 μm nylon syringe filter (Fisher), and stored as frozen aliquots. Matrix metalloproteinase (MMP)-degradable PEG hydrogels were formed using an amino acid sequence modified from a native collagen sequence (Nagase et al., Biopolymers 40(4):399-416 (1996)) (KCGPQG~IWGQCK (SEQ ID NO:1); Active sequence in bold, cleave site=(~); Genscript, >90% purity, C-terminus amidated), with cysteines on each end to cross-link 8-arm PEG-norbornene molecules. Cell adhesion was promoted by incorporating CRGDS peptide (SEQ ID NO:2) (2 mM final monomer solution concentration; Genscript, >90% purity, C-terminus amidated), an amino acid sequence derived from fibronectin (Pierschbacher et al., *Nature* 309

US 12,649,906 B2

21

(5963):30-33 (1984)). Stock MMP-peptide (~75 mM peptide/150 mM SH) and CRGDS peptide (~100 mM) solutions were prepared and sterile filtered through a 0.22 μm low protein binding polyvinylidene difluoride (PVDF) syringe filter (Millex) and the final concentration was verified after filtration using an Elman's assay (Thermo Scientific; modification of Manufacturer's protocol: PBS used to dissolve all reagents).

Figures 2A, 2B, 2C, 2D:
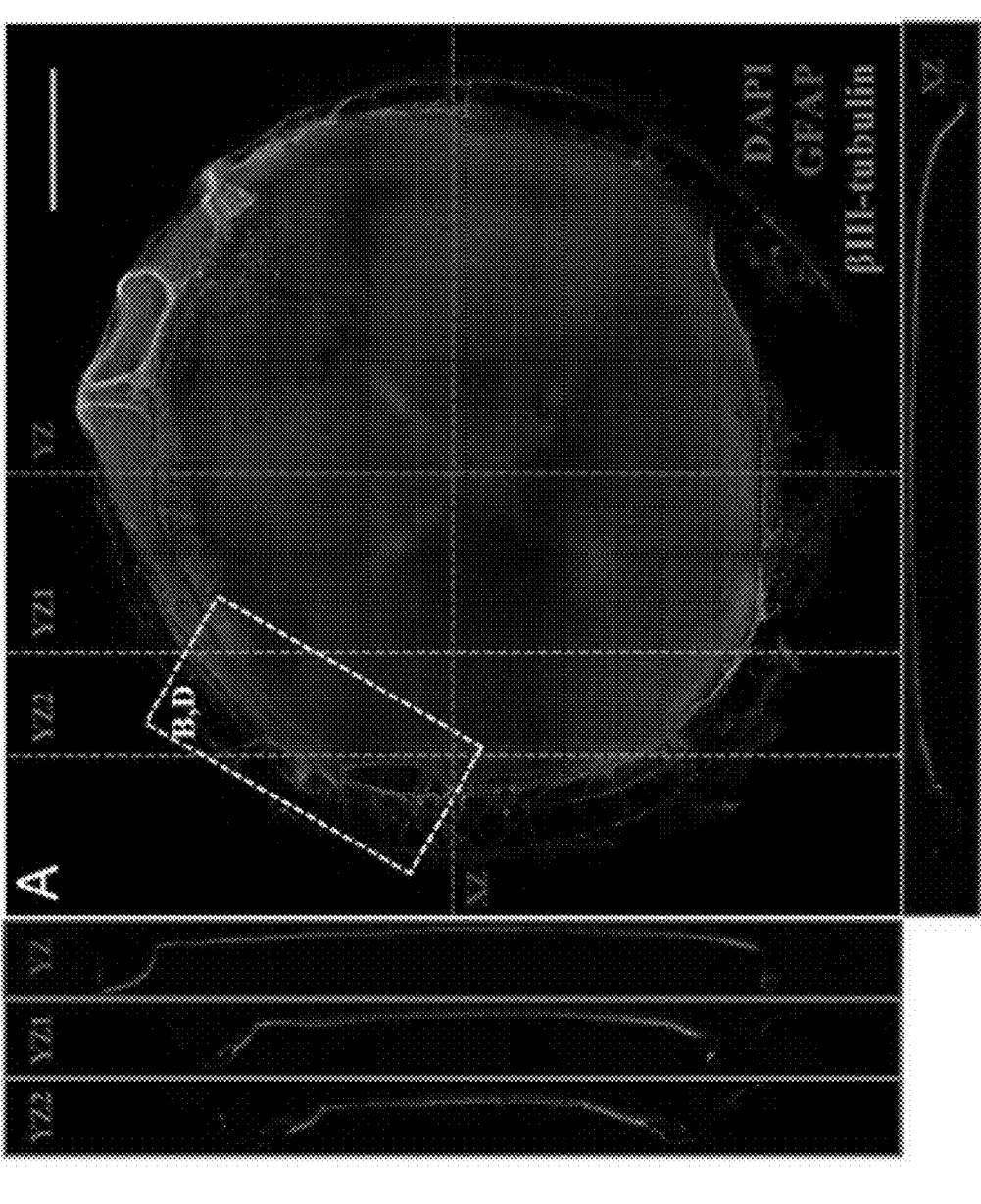
FIGS. 2A-2D are images demonstrating morphological characteristics of neural constructs. Human embryonic stem cell-derived precursor cells were co-cultured on polyethylene glycol (PEG) hydrogels in 24-well Transwell inserts. Neural progenitor cells (NPCs) were seeded on synthetic PEG hydrogels (day 0), followed by endothelial cells (ECs) and mesenchymal stem cells (MSCs) at day 9 and microglia/macrophage precursors (MGs) at day 13. (A and B) Maximum projection Z stack (525-μm thickness) and slice views (NIS Elements) illustrating βIII-tubulin (green), GFAP (red), and DAPI (blue) for a day 21 neural construct. XZ and YZ cross-sections are illustrated in the regions indicated by dashed lines. The boxed region in A is illustrated in B. (C and D) Volume view images (NIS Elements) corresponding to (C) the full neural construct shown in A (6,300 μm×6,300 μm×550 μm) and (D) the region shown in B (1,570 μm×2, 290 μm×300 μm). (Scale bar in A, 1,000 μm and B, 500 μm).
Figures 3A, 3B, 3C, 3D, 3E, 3F, 3G, 3H, 3I:
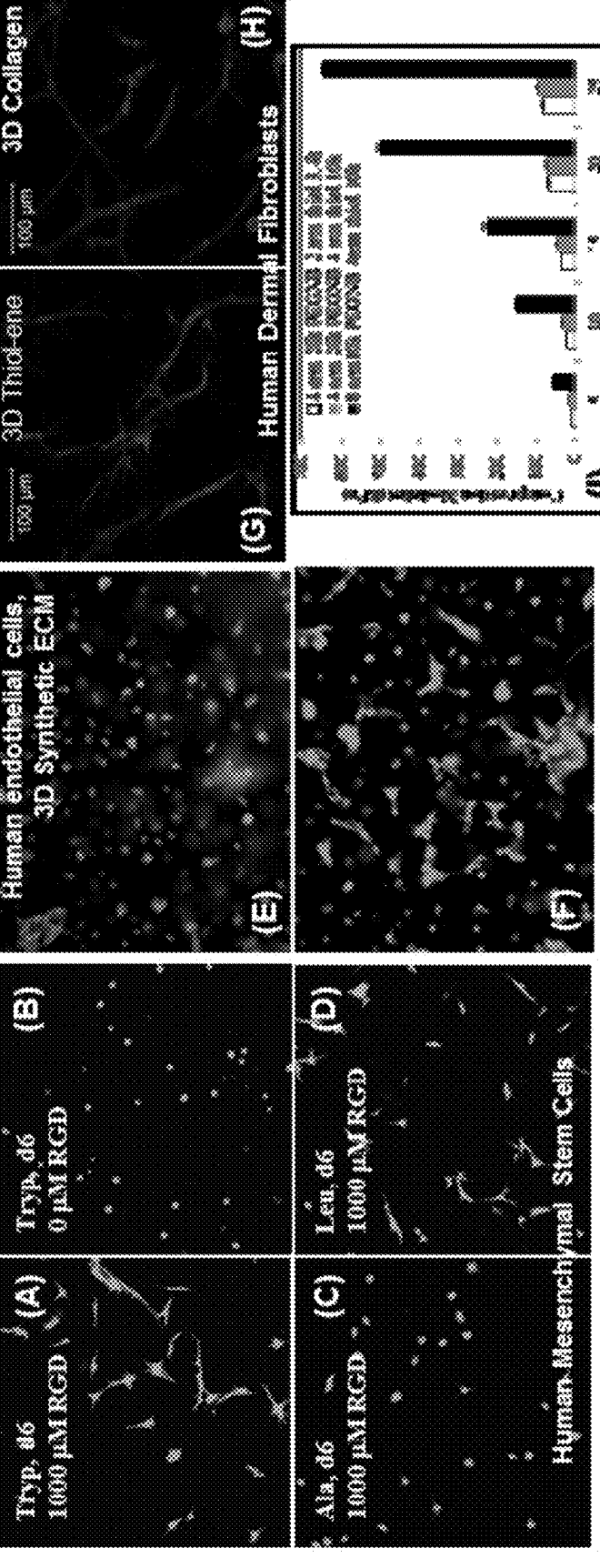
FIGS. 3A-3I are images (A-H) and a graph (I) demonstrating that tunable biophysical and biochemical properties of thiol-ene hydrogels guide cell function.
Figures 5A, 5B, 5C, 5D:
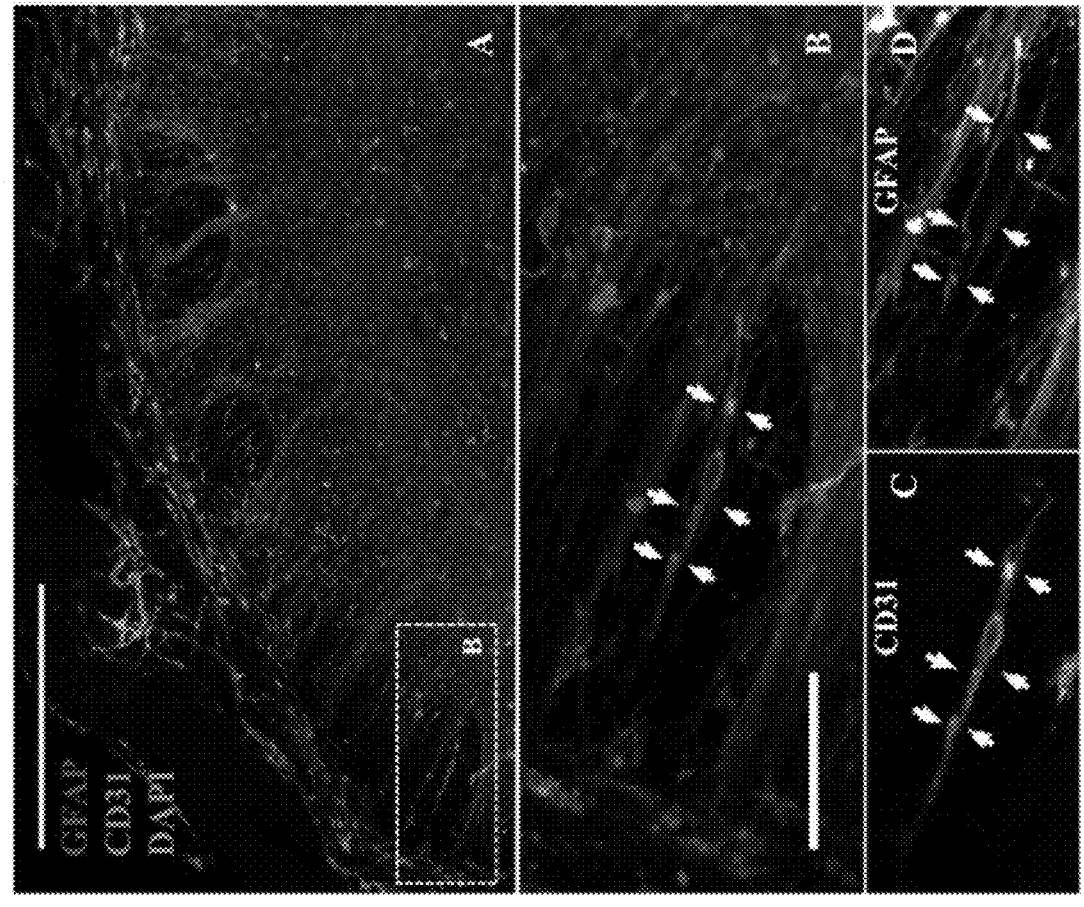
FIGS. 5A-5D demonstrate vascular network formation within neural constructs. (A and B) Immunofluorescence for endothelial cells (CD31, green), glial cells (GFAP, red), and nuclei (DAPI, blue) for a day 21 neural construct. (B) Zoom of the boxed region shown in A to illustrate association and alignment for a capillary tubule and radially oriented glial cells (arrows). The cells in B are shown as single channel grayscale images for (C) CD31 and (D) GFAP. Scale bars in A, 250 μm and B-D, 100 μm (shown in B).

As shown in FIGS. 2A-2D, biophysical and biochemical properties of thiol-ene hydrogels are tunable and influence cell properties. For example, spreading of mesenchymal stem cells (MSCs) is a function of degradation rate and adhesion ligand density. MSC attachment and spreading was tuned by varying adhesion ligand density (using the fibronectin mimic CRGDS) or the susceptibility of the crosslinker to proteolytic degradation (by varying the P'$_2$ position of the amino acid sequence). MSC spreading was maximized with Tryptophan (W) in the P'2 position of the amino acid sequence and 1000 mM RGD (FIG. 2A), while MSCs remained rounded in hydrogels having the most degradable crosslinker (Tryptophan in the P'2 position) but lacking an active adhesion peptide (FIG. 2B). Only limited spreading was observed when Tryptophan was replaced with Ala due to lower susceptibility to MMP degradation (FIG. 2C), while intermediate spreading was observed when Tryptophan was replaced with Leucine (FIG. 2D). Human umbilical vein endothelial cells (HUVECs) are viable when grown in 3D synthetic extracellular matrices, but the presence of different RGD concentrations affected 3D organization (FIGS. 2C-2D). Human dermal fibroblasts grown in 3D synthetic matrix (relative to growth on collagen) demonstrate that the basic morphology and cytoskeletal structure of the resulting tissue constructs is indistinguishable from natural extracellular matrices. It was also observed that cell attachment and spreading of human MSCs in three dimensions are affected by choice of adhesion ligand density and proteolytically degradable crosslinker.

For subsequent assays, the final monomer formulation for PEG hydrogels was 40 mg/mL 8-arm PEG-NB, 4.8 mM MMP-peptide crosslinker (9.6 mM cysteines, 60% molar ratio relative to norbornene arms), 2 mM CRGDS (SEQ ID NO:2), and 0.05% (wt/wt) Irgacure® 2959 photoinitiator (BASF Schweiz AG, Basel, Switzerland). Hydrogels were formed by pipetting 30 μL monomer into 24-well BD Transwell inserts (1 μm pores, Fisher; Quality control experiments) or 40 μL into Corning IITS Transwell-24 well permeable support (0.4 μm pores, Sigma Aldrich; Toxicity experiments). After pipetting, any gaps between the PEG monomer solution and the edge of the insert (due to surface tension) were removed by tilting the insert plate and gently tapping until the solution uniformly covered the bottom of the transwell insert membrane. Transwell plates containing inserts and monomer solutions were placed on the top shelf of a UVP XX-15 lamp stand (Fisher) and exposed to ~365 nm centered UV light (UVP XX-15L lamp, Fisher) for 2.5 minutes. After polymerization, hydrogels were incubated in DF3S medium overnight to allow swelling and equilibration (5% CO$_2$, 37° C.).

Seeding Porous Biomaterials With Pluripotent Stem Cell-Derived Neural Progenitor Cells: Vascularized neural tissue constructs were obtained according to the strategy generally depicted in FIG. 1B. Neural and astrocyte precursors were overlayed onto the cell-embedded PEG hydrogel and cultured for about two weeks. Specifically, cryopreserved neural progenitor cells (NPCs) were thawed and expanded on 6-well plates coated with Matrigel® (BD Biosciences, 0.5 mg per plate for at least 1 hour) and cultured in neural expansion medium. One vial of frozen NPCs (~1.2×10$^7$ cells) were thawed and plated in 3 wells of a Matrigel® coated 6-well plate (2 vials were thawed in one Matrigel® coated 10 cm dish), cultured for 2-3 days (depending on initial confluence) and passaged 1:3 using Accutase™. NPCs were passaged 1:3 after 2 days of additional culture, expanded for 2-3 more days and used for experiments. NPCs were removed from the plate using 1 mL Accutase/well, from which an aliquot was removed for counting. After adding the appropriate volume of cell suspension to a conical vial, NPCs were pelleted at 0.2G for 4 minutes. NPCs were resuspended and seeded in neural expansion medium at a density of 100,000 cells/24-well insert. NPCs were allowed to attach overnight, and then neural expansion medium was exchanged on Day 1 and every 2 days for the remainder of the experiment. For each medium exchange, all medium under the insert was aspirated, while approximately ¾ of the medium was removed from the top by sliding the pipette tip down the side of the well to avoid damaging the developing neural tissue constructs.

As described in the following sections, the resulting vascularized neural tissue construct mimics in vivo cephalic mesenchyme-neural epithelial interactions. neural progenitor cells and/or components derived from such progenitors are introduced by adding the components to the top of a three-dimensional tissue construct.

Differentiation and growth of Pluripotent Stem Cell-Derived Endothelial Cells (ECs) and Mesenchymal Stem Cells (MSCs): Endothelial cells were expanded from cryopreserved stocks on fibronectin-coated plates (Life Technologies, 100 μg per plate) using E7BV media, with one vial (1×10$^6$ cells) per 6 wells of a 6-well plate or a single 10 cm dish. ECs were split 1:3 after 2 days using Accutase, cultured for an additional 3 days, and then used for experiments. E8BA medium: E8 supplemented with BMP4 (5 μg/L) and Activin A (25 μg/L). E7V medium: E8 minus TGFβ1, supplemented with VEGF-A (50 μg/L). E7BVi medium: E7V supplemented with BMP4 (50 μg/L) and SB431542 (5 TGFβ inhibitor) (Inman et al., *Mol Pharmacol* 62(1):65-74 (2002)).

At day 9, ECs and MSCs were seeded on top of the differentiating NPC layer at a total density of 100,000 cells/well, with a 5:1 ratio of ECs:MSCs (83.3K:16.7K). Both ECs and MSCs were harvested using Accutase and counted before centrifugation. Cells were counted and mixed in the appropriate ratio, centrifuged, and resuspended for seeding. Neural expansion medium was exchanged on day 11 (2 days after seeding ECs and MSCs). At day 13, microglia/macrophage precursors were harvested and seeded at a density of 100,000 cells/insert. Neural expansion medium was exchanged on day 14, and then every other day until samples were collected for RNA, sorting, or immunofluorescence imaging.

Addition of Primitive Macrophages to Neural Constructs: Primitive macrophages were added to hydrogel neural tissue constructs after initial vascular network organization and after neural progenitor cells had self-assembled into multi-layered structures with radially organized neural and glial populations (see FIG. 8) reminiscent of the early neuroepithelium.

The neuronal tissue constructs were characterized by several features that resembled the human neocortex during early development of the cortical plate.

Immunofluorescence imaging and RNA-sequencing provided evidence for diverse neuronal and glial phenotypes, including interneurons and projection neurons (FIGS. 3A-3I). Radially oriented GFAP⁺ and Vimentin⁺ cells were consistent with radial glia, and a densely packed cellular layer characterized by stratification of cortical neurons resembled features of the mammalian cortex, such as previously reported for human pluripotent stem cell-derived 3D in vitro neuronal tissues (Lancaster et al., *Nature* 501:373 (2013); Kadoshima et al., *Proc. Natl. Acad. Sci. U S. A.* 110:20284 (2013); Mariani et al., *Proc. Natl. Acad. Sci.* 109:12770 (2012); Eiraku et al., *Cell Stem Cell* 3:519 (2008)). For example, a reelie layer at the outer tissue edge and an adjacent layer abundant with calretinin+neurons assembled similarly to Cajal-Rezius neurons in the marginal zone and interneurons of the emerging human cortical plate at ~7-9 gestational weeks (GW).

In summary, our neuronal constructs were characterized by cortical organization and stratification that was consistent with 3D neuronal tissues in vitro and features described for the human neocortex during development. Importantly, it is our understanding that these neuronal tissue constructs provide the first in vitro model of human cortical development that was formed using a synthetic hydrogel (rather than Matrigel or suspension culture) and that, in some embodiments, comprises microglia derived from human pluripotent stem cells. Moreover, the neuronal tissue constructs described herein are believed to be the first to incorporate vasculature, to be formed using methods that can be easily automated or scaled for high throughput protocols, and, as described in the following Example, the first in vitro three-dimensional neural "organoids" useful for quantitative toxicity screening and for successfully predicting neural toxicity (in a blinded study).

Figures 4A, 4B, 4C, 4D, 4E, 4F, 4G, 4H, 4I, 4J, 4K:
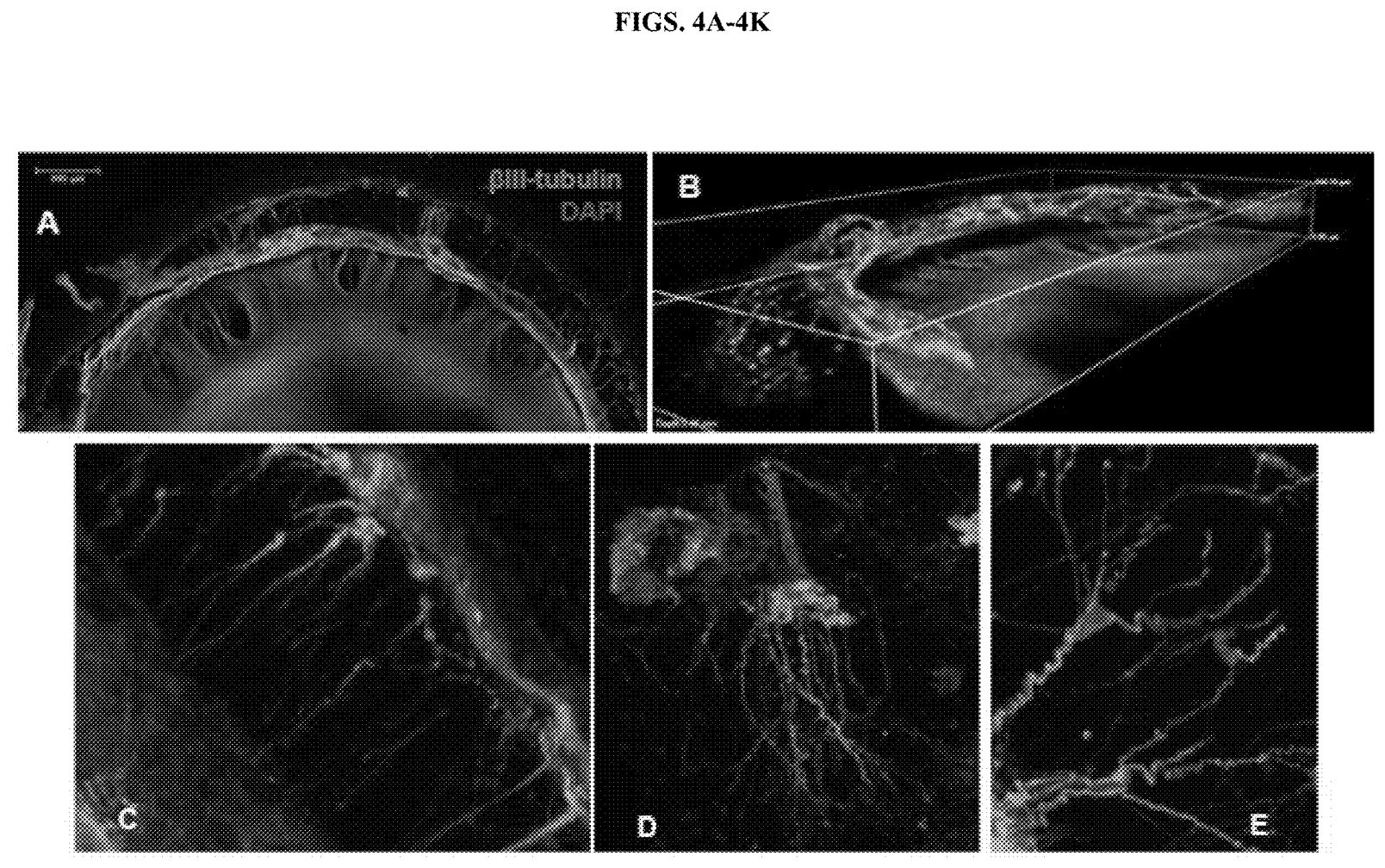

The timing for vascularization of the human cerebral cortex parallels emergence of the cortical plate, when angiogenic sprouts from the pial capillary plexus begin penetrating the neural tube. Endothelial cells formed extensive vascular networks by day 16 (FIGS. 4A-4C), while capillary-like structure was more organized and extended throughout the neuronal constructs by day 21 (FIGS. 4D-4F). Vascular networks penetrated into the layered regions and extended around the circumference of the neuronal constructs (FIGS. 4E-4F), and both mesenchymal (FIG. 4G) and glial (FIG. 4H) cells wrapped capillary-like tubules and larger vessel-like structures on the periphery. Further, capillary-like tubules aligned with radial glia (FIG. 4I), especially at the leading edge of the extending vascular network (FIG. 4K). Glial cells attached to capillary-like tubules through end-feet (FIGS. 4J-4K), suggesting that the neuronal constructs mimicked at least some aspects of the blood-brain-barrier (BBB). By day 21, the constructs contained an extensive neural network, cells exhibiting neural and glial phenotypes, interconnected capillary networks, and microglia-like cells. Notably, vascular network formation was induced within the neuronal constructs without the requirement for exogenous addition of growth factors such as VEGF. Further, RNA-sequencing demonstrated that genes for several blood vessel-promoting growth factors were highly expressed within the neuronal constructs for control samples without vascular cells (e.g., VEGFA and PDGFB). Therefore, cellular signaling within the neuronal construct provided the necessary cues to induce vascularization, which is consistent with initial recruitment of capillaries to the cerebral cortex by the neuroepithelium.

Several microglia genes were expressed only after primitive macrophages were added to the neuronal constructs (e.g., AIF1/IBA1, TREM2). Further, IBA1+ (AIF1) cells with ramified morphologies were distributed throughout the neuronal constructs by day 21 (FIGS. 5A-5D), which is consistent with microglia in the resting state. Some IBA1+ cells also interacted with capillary-like tubules within the neuronal constructs (FIGS. 5B-5C), which has been observed during human development and may indicate a role for microglia in guiding vascular organization. Therefore, the 3D neuronal constructs provided the necessary cues to induce primitive macrophages to adopt a phenotype characterized by several hallmark features of microglia.

RNA sequencing (RNA-Seq) was used to quantitatively assess sample uniformity by comparing differential gene expression for replicate neural constructs after 14 and 21 days of differentiation on hydrogels. In addition, replicate samples were characterized by Spearman's correlation coefficients ($\rho$)≥0.99 to at least 21 days of differentiation. RNA-Seq revealed an increase in expression of CD68, a microglial cell marker. RNA-Seq also identified several characteristic microglia genes that were detectable only when primitive macrophages/microglia precursor cells were incorporated into the neural constructs, such as CD11B (ITGAM), TREM2, and IBA1 (AIF1). See FIGS. 7A-7C and Tables 2 and 3. RNA-Seq identified differentially expressed genes for day-21 neural constructs compared to H1 ES cells (in normal culture), and characteristic gene ontology (GO) clusters were identified from the resulting gene sets using the DAVID functional annotation database (Huang et al., *Nat. Protocols* 4(1):44-57 (2008); Ashburner et al., *Nature Genet.* 25:29-29 (2000)). Neural constructs were characterized by 4865 upregulated and 4669 down-regulated genes relative to H1 ES cells (FDR≤0.005). Upregulated genes for the neural constructs were enriched within GO categories that included neuron differentiation (GO:0030182, 212 genes), forebrain development (GO:0030900, 52), hindbrain development (GO:0030902, 31), synaptic transmission (GO:0007268, 143), vasculature development (GO:0001944, 85 genes), and others. A wide variety of expressed genes within the neural constructs have previously been identified for roles in human cortical layering, including marginal zone and layer I neurons (GAP43, Reelin/RELN and Calretinin/CAL132), upper layer neurons (e.g., CUX1, SATB1), and deep layer neurons (e.g., CTIP2/BCL11B, ETV1, FOXP1, SOX5) (Bayatti et al., *Cereb. Cortex* 18(7):1536-1548 (2008); Meyer et al., *J. Neurosci.* 20(5):1858-1868 (2000); Zecevic et al., *The Journal of Comparative Neurology* 412(2):241-254 (1999); Saito et al., *Cereb. Cortex* 21(3):588-596 (2011); Ip et cd., *Cereb. Cortex* 21(6):1395-1407 (2011). Therefore, RNA-seq identified diverse cellular phenotypes within the neural constructs and suggested a role for neurodevelopmental mechanisms in the emergence complexity within the tissue.

Iba-I protein expression was detected by fluorescent antibody staining. Iba1+ cells were distributed throughout the neural constructs by day 21, and adopted ramified morphologies, which is a distinguishing feature for microglia in the resting state. Iba1+ cells associated with endothelial tubules, which has been observed during human development and suggests a possible role for microglia in guiding vascular organization within the neural constructs. Therefore, human ES cell-derived primitive macrophages exhibit several properties consistent with a microglia-like phenotype observed within the neural constructs.

Figures 6A, 6B:
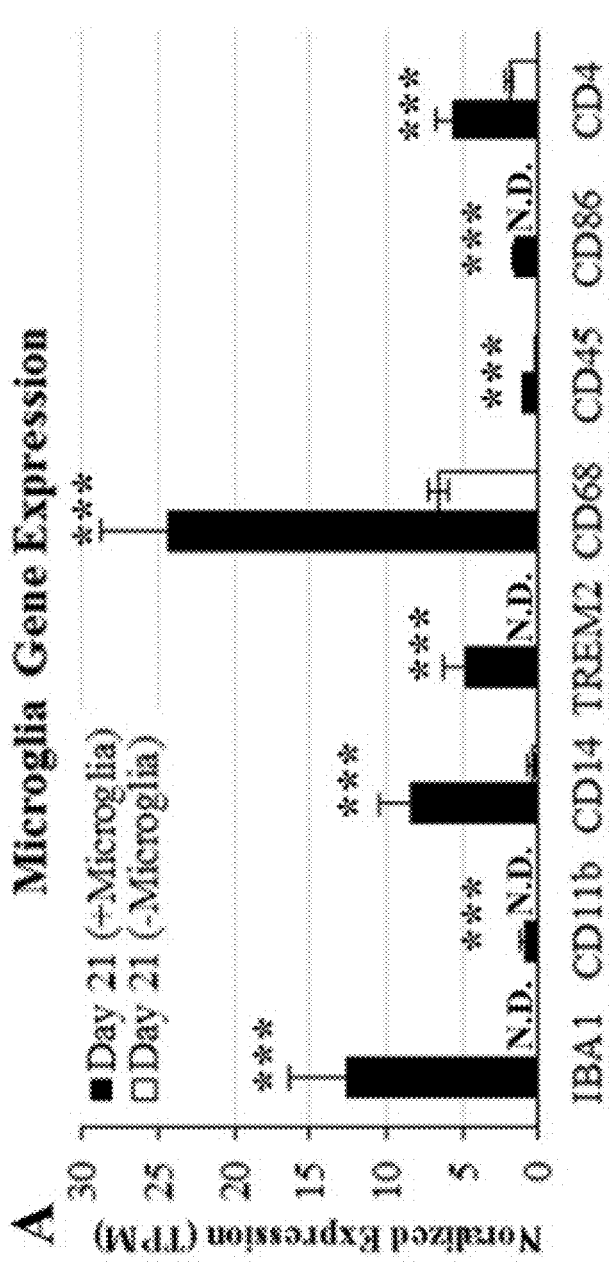
FIGS. 6A-6B demonstrate incorporation of microglia into neural constructs. (A) Gene expression for neural constructs

Human ES cell-derived neural progenitor cells alone self-assembled into multilayered tissue-like structures when cultured on degradable biomaterials such as MMP-degradable PEG hydrogels (FIGS. 6A-6B) whereas self-organization was less pronounced on non-degradable hydrogels, demonstrating that remodeling of the hydrogel components influences the self-assembly and organization of neural progenitor cells into three-dimensional tissues. It is important to note that both degradable and non-degradable hydrogel construct formats are useful for studying the effect of altering material properties of the construct on the cells and tissues within the construct. In addition, the physical and chemical properties of the two formats may be beneficial for particular screening applications and other uses as described herein.

In sum, these data demonstrate that three-dimensional multilayered neural tissue-like constructs can be produced with remarkable uniformity when ES cell-derived precursor cells are cultured on bioactive hydrogels.

TABLE 2

| Gene Expression in Neural Constructs | | | | |
|---|---|---|---|---|
| | Average | | Standard Deviation | |
| Genes | Day 16 | Day 21 | Day 16 | Day 21 |
| AIF1/IBA1 | 12.1 | 15.6 | 3.3 | 8.8 |
| ITGAM/CD | 2.3 | 1.2 | 0.6 | 1.2 |
| PTPRC | 4.1 | 3.6 | 0.9 | 3.3 |
| CX3CR1 | 3.8 | 3.7 | 0.8 | 4.6 |
| CD68 | 17.3 | 23.8 | 4.0 | 18.9 |
| CD14 | 1.8 | 3.0 | 1.6 | 1.4 |

Normalized expression (TPM; N = 4)

Example 2—Methods and Materials

Human Embryonic Stem (ES) Cell Culture

Essential 8 (E8) medium (1): DMEM/F12 HEPES (Life Technologies, 11330-032), L-ascorbic acid-2-phosphate magnesium (64 mg/L; Sigma-Aldrich, A8960-5G), sodium selenite (14 µg/L; Sigma-Aldrich, S5261), NaHCO3 (543 mg/L), holo-transferrin (10.7 mg/L; Sigma-Aldrich, T0665-1G), insulin (20 mg/L; Sigma-Aldrich, 19278), human recombinant FGF2 (rhFGF2, 100 µg/L), and TGFβ1 (2 µg/L; R&D Systems, 240-B-001MG/CF).

H1 human embryonic stem (ES) cells were maintained in E8 medium (1) (Life Technologies) on Matrigel (growth factor reduced, Corning 356230) coated culture plates and were passaged with 0.5 mM EDTA in 1×PBS as previously described (2). Cells were karyotyped within 10 passages and tested negative for mycoplasma contamination.

Human ES Cell Differentiation into Neuralprogenitor Cells (NPCs)

DF3S medium: DMEM/F-12, L-ascorbic acid-2-phosphate magnesium (64 mg/L), sodium selenium (14 µg/L), and NaHCO3 (543 mg/L).

Essential 6 (E6) medium: DMEM/F-12, L-ascorbic acid-2-phosphate magnesium (64 mg/L), sodium selenite (14 µg/L), NaHCO3 (543 mg/L), transferrin (10.7 mg/L), and insulin (20 mg/L).

Neural expansion medium: DF3S medium supplemented with rhFGF2 (5 µg/L), 1× N2 (Life Technologies, 17502-048) and 1× B27 (Life Technologies, 17504-044) supplements.

The procedure for deriving neural progenitor cells was modified from a previously reported protocol (3). H1 ES cells were split using 0.5 mM EDTA in 1×PBS and cultured in E6 medium supplemented with rhFGF2 (100 µg/L) and SB431542 (TGF-β receptor inhibitor, 10 µM; Sigma-Aldrich). After two days, the medium was switched to E6 medium supplemented with SB431542 (10 µM) for seven days with daily media exchange to induce the formation of neural rosettes. The neural rosettes were then mechanically dissociated from the culture dish and cultured as floating aggregates in neural expansion medium for four days. Aggregates were then dissociated with Accutase (Life Technologies) and plated onto Matrigel (growth factor reduced, Corning 356230) coated plates in neural expansion medium. Cells were cultured for an additional 22 days and passaged when confluent, yielding >90% SOX1+/βIII-tubulin+neural progenitor cells ("NPCs"). NPCs were cryopreserved at 1.2×107 cells per vial. Cryopreserved neural progenitor cells were used for subsequent expansion and formation of 3D neural constructs to ensure a uniform cell source for all experiments.

Human ES Cell Differentiation into Endothelial Cells (ECs)

E8BA medium: E8 medium supplemented with BMP4 (5 µg/L) and Activin A (25 µg/L).

E7V medium: E8 medium minus TGFβ1, supplemented with VEGF-A (50 µg/L).

E7BVi medium: E7V supplemented with BMP4 (50 µg/L) and SB431542 (5 µM, TGFβ inhibitor)(4).

H1 ES cells (80-90% confluent) were dissociated using TrypLE (Invitrogen) for three minutes at 37° C. and plated 1:3 on vitronectin-coated plates (60 µg/10 cm dish, VTN-N, Life Technologies)(1). ES cells were first cultured for two days (to 100% confluence) in E8BA medium, which was supplemented with 10 µM Y-27632 for the first day to improve cell survival during attachment. It is critical to achieve 100% cell confluence by day 2 to ensure highly efficient differentiation. Cells were then cultured in E7BVi medium for an additional three days. Endothelial cells were then isolated with CD34 microbeads (Miltenyi) by autoMACS (Miltenyi) to yield purified populations of CD34+/CD31+ cells ("ECs"). The purified endothelial cells were either cryopreserved immediately or cultured on fibronectin-coated plates in E7V medium for one passage before cryopreservation.

Human ES Cell Differentiation into Mesenchymal Stem Cells (MSC)

Mesenchymal serum-free expansion medium (M-SFEM): 50% StemLine II serum-free HSC expansion medium (HS-FEM; Sigma-Aldrich), 50% human endothelial serum-free medium (ESFM; Invitrogen), GlutaMAX (1/100 dilution; Invitrogen), Ex-Cyte supplement (1/2000 dilution; Millipore), 100 mM monothioglycerol (MTG), and 10 µg/L rhFGF2.

Mesenchymal stem cells (MSCs) were derived from H1 ES cells using a previously published protocol (5). Tissue culture polystyrene plates were coated with human fibronectin (5 mg/mL; Invitrogen) and human collagen I (10 mg/mL; BD Biosciences) in phosphate buffered saline (PBS) for expansion and Accutase (StemPro) was used for passaging. MSCs were expanded for five passages in M-SFEM (5), followed by two passages in pericyte medium (ScienCell), and then cryopreserved (PDGFRB+CD13+, "MSCs").

Human ES Cell Differentiation into Microglia/Macrophage Precursors (MG)

Microglia/macrophage precursors were produced using feeder-free conditions by modifying a previous protocol for differentiating H1 ES cells down mesendoderm and hemogenic endothelium lineages (see Uenishi et al. (2014) Stem Cell Rep 3(6):1073-1084). 6-well plates were first coated with 40 µg Tenascin C overnight at 4° C. Tenascin C plates were rinsed with PBS, and then seeded with singularized H1 ES cells at a density of 62,500 cells/cm$^2$ in E8 medium+10 µM Y-27632 (ROCK inhibitor, R&D Systems). Cells were cultured for 24 hours under normoxic conditions.

Initiate early mesoderm differentiation. 24 hours after plating H1 ES cells, E8 media was aspirated and replaced with DM1+1 µM Y-27632. Cells were then cultured under hypoxic conditions (5% O$_2$) for two days (do not expose cells to normoxia). During the two days of culture, cells detach and reattach. It is important that the culture is not disturbed, as cells will aggregate in the middle of the plate, affecting differentiation efficiency.

Continue hematovascular mesoderm differentiation. On day two, the culture was checked for surviving cell clumps that had not fully reattached. If non-adherent cells were present, a 10 mL pipette tip was used to gently pull media off plate, and the non-adherent cells and cell clumps were centrifuged at 300×g for five minutes to form a pellet. DM1 was aspirated from the pellet, and the cells were resuspended in DM2. Cells were gently plated back into same plate, and culture was continued in a hypoxic incubator. If only debris was present, DM1 was aspirated and DM2 was added slowly as to not disrupt the adherent cells. Culture was continued in a hypoxic incubator.

Differentiate and expand hemogenic endothelial cells into hematopoietic progenitor cells (HPCs). On day 4, DM2 medium was aspirated and replaced with DM3 medium. Culture was continued under normoxic conditions. On day 6 of culture (two days after adding DM3 media), additional DM3 media was added without aspirating media already present. Culture was continued in a normoxic incubator. Cell cultures were expanded for an additional 3-5 days in DM3 (longer time is required when cells not fully adherent after hematovascular differentiation). If media color indicated a significant pH drop, half of the media volume was removed from the plate and placed into a low attachment dish. An additional volume of DM3 (1:1 mix of old and fresh media) was added to both culture plates. After 3-5 days, spent media containing non-adherent HPCs was collected and centrifuged at 300×g for about five minutes to pellet.

Myeloid progenitor (MP) differentiation. Expansion was continued in myeloid progenitor medium DM4, where 1×10$^6$ HPCs/mL were to a low attachment culture dish under normoxic conditions. At this point, the cells could be grown in a 10 cm dish under normoxic conditions. Cells were expanded for 2-5 days in the DM4 medium. At least five days in culture was required for proper transition to macrophages, but no more than five days. DM4 was added if the culture's pH significantly dropped (half/half mixture; do not transfer cells). Up to 2×10$^7$ cells were obtained from a 10 cm dish. During expansion in DM4 medium (2-5 days), non-adherent cells were collected for sorting to identify CD34$^+$ and CD45$^+$ cells.

Microglia/macrophage precursor (MG) differentiation. After 2-5 days of myeloid progenitor expansion, 5×10$^5$ non-adherent cells were added to macrophage differentiation medium DM5 in a 10 cm tissue culture treated dish. Cells were cultured for three days, then an equivalent volume of DM5 media was added without aspiration of the media. After five days (two additional days in DM5), ~50-70% of cells had attached. When cells reached ~70-80% confluence (adherent cells), remaining non-adherent cells were transferred to a new 10 cm dish to promote adhesion. Both adherent and non-adherent populations are CD45$^+$, but non-adherent cells will be CD14$^{Low/Negative}$ and adherent cells will be CD11b$^+$/CD14$^+$. On days 5-10, non-adherent cells began to attach and differentia into CD11b$^+$ and CD14$^+$ cells. Culture in DM5 medium was continued.

For the quality control assays, RNA was collected on days 14 and 21. For the 3D toxicity screening experiments, RNA was collected on days 16 and 21 (permitting 2 days of chemical exposure before collecting at the first time point).

Immunofluorescence imaging: Blocking buffer: 0.25% Triton X-100 and 1% BSA in PBS; Incubation buffer: 0.05% Triton X-100 and 1% BSA in PBS; Rinse buffer: 0.05% Triton X-100 in PBS.

Primary Antibodies: Rabbit anti-β3-tubulin (1:500; Cell Signaling, mAb #5568S), mouse anti-β3-tubulin (1:500; R&D Systems, MAB1195), rabbit anti-calretinin (1:100-1:200: Abcam, ab137878), rabbit anti-GABA (1:200: Abcam, ab43865), rabbit polyclonal anti-glial fibrillary acidic protein (GFAP) (1:500; Dako, Z033401-2), goat anti-glial fibrillary acidic protein (GFAP) (1:100-1:200; C-19; sc-6170, Santa Cruz Biotechnology), mouse anti-phospho-vimentin (1:200; S55 [4A4]; Abcam, ab22651), mouse anti-CD31 (1:200; Endothelial Cell, Clone JC70A; DAKO, M082301-2), mouse anti-O4 (1:100-1:200; clone 81; Millipore, MAB345), Chicken polyclonal anti-Tbr1 (1:100-1:200; Millipore, AB2261), mouse anti-SOX-2 (Cell Signaling, mAb #4900S), rabbit anti-SOX-2 (Cell Signaling, mAb #3579S), mouse anti-MAP2, (clone AP20; Millipore, MAB3418), mouse anti-Reelin (1:100; clone G10, a.a. 164-496; Millipore, MAB5364), mouse anti-Brn-2 (POU3F2) (1:200; clone 8C4.2; Millipore, MABD51), rabbit anti-Brn-2 (POU3F2) (1:200; Cell Signaling, mAb #12137S), rabbit anti-Ctip2 (Bcl-11b) (1:200; Cell Signaling, mAb #12120S), rabbit anti-VGLUT2 (1:100; Abeam), mouse anti-MAP2 (1:500; clone AP20; Millipore, MAB3418), goat anti-Iba1 (1:100; Abeam, ab5076), rabbit anti-Tyrosine Hydroxylase (Cell Signaling, mAb ##2792S), rabbit anti-PDGFR-α (1:100; Santa Cruz Biotechnology, sc-338).

Secondary Antibodies: Alexa Fluor secondary antibodies were used for all experiments (Life Technologies): Donkey anti-goat 568 (A11057) or 647 (A21447); Donkey anti-rabbit 488 (A21206), 568 (A10042), or 647 (A-31573); Donkey anti-mouse 488 (A-21202), 568 (A10037), or 647 (A31571); Goat anti-chicken (A11041).

Immunostaining full neural constructs: All steps for immunostaining were performed within transwell inserts. Neural constructs were fixed for 60 min. using 2% buffered formalin and then rinsed with PBS (or stored at 4° C. until immunostaining). Neural constructs were permeabilized and blocked in blocking buffer (at least 60 min.). For some experiments, blocking buffer was used for all steps until final rinse, with similar results. Primary antibodies were prepared in incubation buffer, added to the neural constructs, and incubated overnight at 4° C. Neural constructs were then rinsed (2× with rinse buffer, at least 60 min./ea.) followed by a third rinse step (blocking buffer, at least 60 min.). Secondary antibodies and 1:1000 DAPI (Sigma) were prepared in incubation buffer, added to the neural constructs, and incubated overnight at 4° C. (or at least 4 hours at room temperature). Neural constructs were rinsed 2×60 min. in rinse buffer, followed by an overnight rinse at 4° C. in incubation buffer. Samples were then stored in PBS until further processing (typically at least 24 hours).

Neural constructs were removed from the transwell insert by cutting the bottom edge of the membrane, separated from the membrane, and mounted in aqua polymount solution (Polysciences, Inc.) on the bottom of a 35 mm glass bottom dish (MatTek). To limit bubble formation in the mounting solution, a thin layer was first added to the glass bottom of the 35 mm dish. The neural construct was usually placed face down into the layer of mounting solution (with some samples placed face up), after which a drop of mounting solution was added to cover the construct. A coverslip was then dropped onto the neural construct in mounting solution and allowed to settle, rotating the dish to ensure uniform coverage of the mounting solution under the coverslip. The coverslip was allowed to settle overnight at 4° C., and sealed around the edges with fingernail sealant. The samples remained stable for imaging for at least 1 month.

Immunostaining cryopreserved sections: Neural constructs were fixed in the transwell insert for 60 min. using 2% buffered formalin and rinsed with PBS (overnight at 4° C.). The samples were then rinsed in 15% Sucrose/PBS (at least 24 hours, 4° C.) followed by 30% Sucrose/PBS (at least 24 hours, 4° C.). Neural constructs were removed from the transwell insert by cutting the bottom edge of the membrane, separated from the membrane, and placed face down into cryogel (Tissue-Tek embedding medium), and stored frozen at −80° C. until further processing. Frozen samples were equilibrated to −20° C. and sectioned (20-30 µm sections on glass slides). Glass slides containing sectioned samples were soaked in deionized water for at least 1 hour to remove cryogel. Samples were permeabilized and blocked in blocking buffer for 60 min., rinsed 2×15 min. with rinse buffer, and incubated at room temperature in incubation buffer for at least 60 min. Samples were then treated primary antibodies in incubation buffer at 4° C. (or at least 4 hours at room temperature). Samples were then rinsed with wash buffer (2×15 min.) and incubation buffer (at least 60 minutes, room temperature). Samples were then treated with secondary antibodies and 1:1000 DAPI (Sigma) in incubation buffer overnight at 4° C. (or at least 2 hours at room temperature). Sectioned samples were mounted in aqua polymount solution (Polysciences, Inc.), a glass coverslip was placed over the top, stored overnight at 4° C., and sealed around the edges with fingernail sealant until imaging.

Image processing: Confocal immunofluorescence images were collected using a Nikon AIR confocal microscope. Images were processed using NIS Elements or ImageJ (Rasband 1997-2012, Image J, U.S. National Institutes of Health, Bethesda, Maryland, USA, available at imagej.nih. gov/ij/ on the World Wide Web); Schneider et al., Nat Meth 9(7):671-675. (2012)). Some z-stacks were aligned using the "Align Current ND Document" (NIS Elements) or the StackReg plugin (ImageJ) before creating maximum projection images.

Phagocytosis by microglia/macrophage precursors. Aliquots of zymosan A S. cerevisiae BioParticles® (Texas Red® conjugate; Life Technologies) were prepared in PBS. ~5×106 particles in 500 µL PBS were added to each well of a 6-well plate containing ~400-500K microglia/macrophage precursors in DM5 media. Phagocytosis was imaged over a 24 hour time period (image capture every 10 minutes) using a Nikon Biostation CT.

Flow Cytometry (FACS) Analysis

Flow cytometry analysis was performed on a BD Biosciences FACSCanto II cell analyzer.

Neural Progenitor Cells (NPCs). NPCs were dissociated into single cells with Accutase and fixed with 2% paraformaldehyde in PBS at RT for 10 minutes. Fixed cells were washed once with FACS buffer I (2% FBS in PBS) and permeabilized with ice cold 90% methanol in PBS overnight at −20° C. Fixed and permeabilized cells were then washed once with FACS buffer I and stained with SOX1 (1:100 rabbit anti-SOX1, Cell Signaling) and βIII-tubulin (1:200 mouse anti-βIII-tubulin, R&D systems) primary antibodies overnight at 4° C. followed by conjugated secondary antibodies at RT for one hour. Stained cells were washed once with FACS buffer I and analyzed by flow cytometry.

Endothelial cells (ECs). ECs were dissociated into single cells with Accutase and washed once with FACS buffer I (2% FBS in PBS). Cells were stained with PE-CD31 (1:100; BD Biosciences, 555446) and APC-CD34 (1:100; BD Biosciences, 555824) antibodies in FACS buffer I at 4° C. for 30 minutes. Stained cells were washed once with FACS buffer I and analyzed by flow cytometry.

Mesenchymal stein cells (MSCs). MSCs were dissociated into single cells with Accutase and washed once with FACS buffer I (2% FBS in PBS). Cells were then stained with fluorescently conjugated PE-PDGFR-β and PE-Cy7-CD13 antibodies in FACS buffer I at 4° C. for 30 minutes. Stained cells were then wash once with FACS buffer I and analyzed by flow cytometry.

Microglia/macrophage precursors (MG). Non-adherent cells were first transferred to a conical vial in DM5 medium. Adherent MG were incubated in Accutase, gently removed from the plate using FACS buffer II (0.5% BSA in PBS), and added to the conical vial containing non-adherent cells. The cells were centrifuged (5 minutes at 300×g) and the cell pellet was washed once with FACS buffer II. Cells were then centrifuged (5 minutes at 300×g), resuspended in FACS buffer II, and incubated at 4° C. for 15 minutes for blocking. Cells were centrifuged (5 minutes at 300×g) and resuspended in FACS buffer II with 1:500 PE-CD11b (BD Biosciences, 555388), Alexa Fluor 488-CD14 (BD Biosciences, 562689) and APC-CD45 (BD Biosciences, 555485) and then incubated at 4° C. for 30 minutes (use a shaker plate or invert tube at least three times during incubation). Cells were then washed twice in FACS buffer H and centrifuged (5 minutes at 300×g). Finally, cells were resuspended in FACS buffer II and analyzed by flow cytometry.

Example 3—Predictive Developmental Neurotoxicity Screening In Vitro

For toxicity screening experiments, cells were seeded as described above (Examples 1 and 2), but with 65,000 cells/well for ECs+MSCs (also 5:1 ratio) and 15,000 cells/ well for microglia/macrophage precursors. Neural constructs were treated with non-toxic or toxic compounds starting at day 14, with media exchanged every 2 days. See FIG. 8. The following screening protocol was developed by the Thomson lab. Toxic chemicals (FIG. 10E) were chosen based on previous literature support for neurotoxicity (Adams et al., *Neurotoxicol Teratol* 15(3):193-202 (1993); Cooper et al., *Science* 280(5369):1603-1607 (1998); Crofton et al., *ALTEX-Altera Anim Exp* 28(1):9-15 (2011); Eskes et al. (2003); Grandjean et al., *Lancet Neural.* 13:330 (2014); Lidsky (2003); Radio et al., *Neurotoxicol Teratol* 32(1):25-35 (2010); Zurich (2002)). The screen included the following experimental groups (FIG. 8): (1) construct with neural progenitor cells (NPCs), endothelial cells (ECs), mesenchymal cells (MCs), and primitive macrophages (PMs); (2) construct lacking primitive macrophages (quality control); (3) neural progenitor cells only (quality control).

RNA isolation, cDNA library preparation, and next generation sequencing: The 3D neuronal constructs were lysed directly in the insert by the addition of RLT lysis buffer (Qiagen) and stored at −80° C. until being used for RNA isolation. When total RNA was ready to be extracted, the samples were thawed and 150 μl of the cell lysates in buffer RLT were transferred and re-arrayed to a S-block (Qiagen, Cat. No. 19585) to be mixed with 1 volume of 70% ethanol (the rest of the lysates were stored in the −80° C.). Total RNA was then isolated using Qiagen's RNeasy™ 96 kit beginning with step 3 of the manufacturer's protocol (RNeasy 96 Handbook 01/2002, Using Spin Technology) and included the optional DNase treatment.

Quality control studies: Samples used for quality control were prepared for RNAseq with Illumina's TruSeq™ RNA Sample Preparation Kit v2 following the Low-Throughput (LT) protocol (TruSeq™ RNA Sample Preparation Guide, Part #15008136, Rev. A) using 100 ng of total RNA as input. The cDNA libraries were pooled and run on Illumina's HiSeg™ 2500 with a single read of 51 bp and index read of 7 bp. FASTQ files were generated by CASAVA (v1.8.2). Reads were mapped to the human transcriptome (RefGene v1.1.17) using Bowtie (Langmead et al., *Genome Biol* 10(3):R25 (2009)) (v0.12.8) allowing 2-mismatches and a maximum of 20 multiple hits. The gene expression values (Transcript per Million Reads or TPM) were calculated by RSEM (Li et al., *BMC Bioinformatics* 12:323 (2011)) (v1.2.3).

Toxicity Screening Study: For cDNA preparation for the toxicity screening experiments, mRNA is isolated from purified 100 ng total RNA using Oligo-dT beads (NEB). Isolated mRNA is fragmented in reverse transcription buffer at 85° C. for 7 minutes, and then reverse transcribed with SmartScribe™ reverse transcriptase (Clontech) at 23° C. for 10 minutes followed by a 30 minute incubation at 42° C. with a random hexamer oligo: 5'-CCTTGGCACCCGAGAATTCCANNNNNN-3' (SEQ ID NO:3).

After reverse transcription, RNA is removed by RNaseA and RNaseH treatment. A partial Illumina 5' adaptor (/5phos/ AGATCGGAAGAGCGTCGTGTAGG-GAAAGAGTGTddC) (SEQ ID NO:4) was then ligated to the single stranded cDNA using RNA ligase 1 (NEB) overnight at 22° C. After purification, ligated cDNA was amplified by 18 cycles of PCR using oligos that contain full Illumina adaptors (5'-AATGATACGGCGAC-CACCGAGATCTACACTCTTTCCCTACACGACGC-TCTTCCGAT CT-3'; SEQ ID NO:5) and index primer (5'-CAAGCAGAAGACGGCATACGAGATnnnnnnnnn-nGTGACTGGAGTTCCTTGGCACCC GAGAATTCCA-3' (SEQ ID NO:6); nnnnnnnnnn indicates index nucleotides). The indexed cDNA libraries were pooled and sequenced on an Illumina HiSeq2500 with a single 51 bp read and a 10 bp index read.

RNA-Seq Data Analysis: RSEM expected read counts for each gene were determined by median normalization (utilizing the median normalization function within EB Seqversion 1.5.3) (Leng et al., *Bioinformatics* 29(8):1035-1043 (2013)). EB-Seq (version 1.5.3) was used to calculate FDR for differentially expressed genes (Leng et al., Bioinformatics 29(8):1035-1043 (2013)).

Gene Ontology Analysis: Gene ontology (GO) terms were identified using the Database for Annotation, Visualization and Integrated Discovery (DAVID) (v6.7) functional annotation database (Ashburner et al., *Nature Genet* 25(1):25-29 (2000); Huang et al., *Nat Protocols* 4(1):44-57 (2008)). GO terms were identified by analyzing differentially expressed genes with (FDR≤0.005) and >3-fold upregulated expression for 3D neural constructs relative to H1 ES cells (see Table 3). The following settings were used for DAVID analysis using differentially expressed genes: Gene_Ontology category GOTERM_BP_5; Benjamini corrected p-value≤0.05; Threshold options: Counts=10, EASE=0.05. GO terms were also identified genes with average TPM>16 (N=4, Controls from toxicity experiment) (Dataset S5), which were compared to a combined list of neural, vascular, and glial terms to reduce the total number of genes below 3000 for input into DAVID (combined list and associated GO categories provided in Dataset S7).

Comparisons to Allen Brain Atlas Data: Pairwise Spearman rank correlation was calculated for neural constructs (days 16 and 21, toxicity experiment, N=4), H1 ES cells (N=4), and Allen Brain Atlas data (RNA-seq data only, samples: 8 pcw-40 yrs) (Table 3). Hierarchical clustering is performed by average linkage clustering on those correlations and the distance is 1 minus Spearman correlation.

Machine-Based Learning: We employed linear support vector machines (SVMs) to construct our predictive models (Cortes & Vapnik, *Mach Learn* 20(3):273-297 (1995); Hardin et al., *Stat Appl Genet Mol Biol* 3(1):e10 (2004); Struyf et al., *BMC Genomics* 9:531 (2008); Vapnik VN (1998) *Statistical Learning Theory* (Wiley, New York)), which were described in detail previously (Hardin et al., *Stat Appl Genet Mol Biol* 3(1):e10 (2004); Struyf et al., *BMC Genomics* 9:531 (2008)). We employed SVMs for the following task specification: Given: RNAseq gene expression measurements for roughly 19K genes on one day or on several different days following exposure to various drugs, together with a neural toxicity label on each drug. Do: Construct a model that, from the same type of expression data on a new drug, can accurately identify if the drug is neural toxic.

Evaluations of the approach, including estimates of accuracy and receiver operating characteristic (ROC) curves, were all by hold-out testing, either leave-one-out cross-validation or use of a blinded trial with a single hold-out set (Hardin et al., *Stat Appl Genet Mal Biol* 3(1):e10 (2004); Struyf et al., *BMC Genomics* 9:531 (2008)). A 2-dimensional linear support vector machine (SVM) is illustrated in the plot shown in FIG. 10A, where the hyper-plane reduces to a line that separates the classes (circles) and maximizes the closest points between classes (the support vectors that fix the position and orientation of the hyper-plane). The $x_i$s are the example (circles; genes for the current study), the $y_i$s are their labels (filled or open; toxic or non-toxic for the current study), and w is the weight vector, or vector of coefficients on the features (the dimensions). The red portions in the equation are the additions made for the soft margin version of the SVM (Cortes & Vapnik, *Mach Learn* 20(3):273-297 (1995)), which minimizes the incorrectly classified data points in addition to the margin (di). The linear SVM's output is the weight vector w and the other coefficient b. To make a prediction, the SVM outputs the number $w'x_i - b$, and outputs the label 0 (non-toxic, for our applications) if this number is less than 0, and 1 otherwise. While the numerical output does not have a probabilistic interpretation as does the output of logistic regression, it is common to build a logistic regression model with one input variable (the SVM's output) from the same training set to output a probability (probability of toxic), which we do here.

Leave-one-out cross-validation: Using the leave-one-out cross-validation methodology, we can compute the numbers of true positive (toxic) predictions (TP), as well as false positive (FP), true negative (non-toxic, TN), and false negative predictions (FN). From these we can compute accuracy (fraction of predictions that are correct) as well as the following: Sensitivity (true positive rate, or recall; TP/(TP+FN)), specificity (TN/(TN+FP)), and precision (or positive predictive value; TP/(TP+FP)), as well as other metrics such as F-measure and negative predictive value. Nevertheless, all of these metrics depend on not only the model that produces probabilistic predictions for toxicity but also the probability threshold at which we make positive predictions, such as 0.5. Hence it is common in machine learning and statistical classification to report "thresholdless" curves and or metrics, the most popular being the receiver operating characteristic (ROC) curve and the area under this curve (AUC) such as shown for averaged day 2 and 7 set (FIGS. 9C-9D). The ROC curve plots true positive rate on the y-axis against the false positive rate (1—specificity) on the x-axis as the threshold is varied (shown for averaged training set). Random uniform guessing produces a diagonal from lower left to upper right corner and AUC of 0.5, while perfect prediction produces a graph that goes up to the upper left corner and then across and AUC of 1.0.

For leave-one-out cross validation, there were 60 compounds in the training set and the method proceeds in 60 steps (FIG. 10E). In each step a different data point is held out of the training set, the SVM is trained on the remaining data points, and then it makes its prediction on the held-aside data point. Hence every data point is a test case exactly once, for a model trained without that data point. Results are aggregated over all the folds, or test cases, to estimate how well the SVM model trained on all the data will perform on a new data point (compound). Predictions were made for both replicates for a testing compound and averaged together to generate the final ROC. The AUCs for the training compounds were 0.91 on day 16, 0.88 on day 21, and 0.93 for data averaged from both days. Thus, the SVM for averaged data from days 16 and 21 produced an estimate for future data of 0.93.

Blinded trial: In addition to constructing an SVM model, we also aimed to estimate how well the model predicts the developmental neural toxicities of other compounds. Merely reporting its accuracy on the training set would be overly-optimistic. An unbiased "hold-out testing" method was used to predict toxicity for a RNA-seq data set of ten blinded compounds that were not in the training set (5 toxins, 5 non-toxic controls) but whose neural toxicities were known. After construction and optimization using the training set, the predictive model was then tested on the unknown samples.

As a blinded trial, the assignment of toxins was unknown to researchers generating the SVM model until after the predictions were made. The SVM for averaged day 16 and 21 data was chosen to generate predictive genes from the training set. The SVM produced probabilities which were used to rank the blinded compounds from most likely to least likely toxic, which was then used to produce an ROC curve and compute an AUC ("area under the curve"). In addition, we used a threshold of 0.5 to make definitive predictions, assigning every molecule with probability≤0.5 as "control" and all others "toxic." The AUC generated for the ranking of the blinded set was 0.92, and all compounds except oleic acid were properly assigned as toxic or non-toxic based on the 0.5 probability cutoff. The only error in the ranking was for oleic acid, which was assigned a higher probability of being toxic than L-741,626 and Ouabain. The accuracy of the blinded prediction was 0.9 (9/10 compounds correctly classified), with the only error being the prediction of oleic acid (a control) as a neurotoxin (i.e., a false positive).

REFERENCES

1. D. Rice, S. Barone, *Environ. Health Perspect.* 108, 511 (June, 2000).
2. L. Smirnova, H. T. Hogberg, M. Leist, T. Hartung, *ALTEX-Altern. Anim. Exp.* 31, 129 (2014).
3. P. Grandjean, P. J. Landrigan, *Lancet Neurol.* 13, 330 (March, 2014).
4. L. L. Needham et al., *Environ. Sci. Technol.* 45, 1121 (February, 2011).
5. P. Grandjean, P. J. Landrigan, *Lancet* 368, 2167 (December, 2006).
6. D. C. Bellinger, *Environ. Health Perspect.* 120, 501 (April, 2012).
7. Z. G. Hou et al., *Stem Cell Res. Ther.* 4, S12 (December, 2013).
8. D. V. Hansen et al., *Nat. Neurosci.* 16, 1576 (November, 2013).
9. J. H. Lui, D. V. Hansen, A. R. Kriegstein, *Cell* 146, 18 (July, 2011).
10. P. Rakic, *Nat. Rev. Neurosci.* 10, 724 (October, 2009).
11. I. Bystron, C. Blakemore, P. Rakic, *Nat. Rev. Neurosci.* 9, 110 (February, 2008).
12. M. Marin-Padilla, *Front. Neuroanat.* 6, (September, 2012).
13. M. Marin-Padilla, D. S. Knopman, *J. Neuropathol. Exp. Neurol.* 70, 1060 (December, 2011).
14. J. M. James, Y.-s. Mukouyama, *Semin. Cell Dev. Biol.* 22, 1019 (2011).
15. H. Stolp, A. Neuhaus, R. Sundramoorthi, Z. Molnar, *Front. Psychiatry* 3, (2012).
16. F. Ginhoux, S. Lim, G. Hoeffel, D. Low, T. Huber, *Front. Cell. Neurosci.* 7, (April, 2013).
17. T. Arnold, C. Betsholtz, *Vascular Cell* 5, 4 (2013).
18. H. Kettenmann, U. K. Hanisch, M. Noda, A. Verkhratsky, *Physiol. Rev.* 91, 461 (April, 2011).
19. C. Verney, A. Monier, C. Fallet-Bianco, P. Gressens, *J. Anat.* 217, 436 (October, 2010).
20. A. Monier et al., J. Neuropathol. *Exp. Neurol.* 66, 372 (May, 2007).
21. A. Monier, P. Evrard, P. Gressens, C. Verney, *J. Comp. Neurol.* 499, 565 (December, 2006).
22. J. A. Thomson et al., *Science* 282, 1145 (November, 1998).
23. J. Y. Yu et al., *Science* 318, 1917 (December, 2007).
24. K. Takahashi et al., *Cell* 131, 861 (November, 2007).
25. S. C. Zhang, M. Wernig, I. D. Duncan, O. Brustle, J. A. Thomson, *Nat. Biotechnol.* 19, 1129 (December, 2001).
26. O. Brustle et al., *Science* 285, 754 (July, 30, 1999).
27. M. A. Lancaster et al., *Nature* 501, 373 (September, 2013).
28. J. Mariani et al., *Proceedings of the National Academy of Sciences* 109, 12770 (Jul. 31, 2012, 2012).
29. M. Eiraku et al., *Cell Stem Cell* 3, 519 (November, 2008).
30. M. Ader, E. M. Tanaka, *Curr. Opin. Cell Biol.* 31, 23 (2014).
31. I. Singec et al., *Nat. Methods* 3, 801 (October, 2006).
32. B. D. Fairbanks et al., *Adv. Mater.* 21:5005-5010 (December, 2009).
33. M. Marin-Padilla, *Front. Neuroanat.* 6, (2012-Sep.-13, 2012).
34. P. Rakic, *Cereb. Cortex* 13, 541 (June, 2003).
35. I. Bystron, P. Rakic, Z. Molnar, C. Blakemore, *Nat Neurosci* 9, 880 (2006).
36. G. Meyer, J. P. Schaaps, L. Moreau, A. M. Goffinet, *J. Neurosci.* 20, 1858 (March, 2000).
37. N. Zecevic, A. Milosevic, S. Rakic, M. Marin-Padilla, *The Journal of Comparative Neurology* 412, 241 (1999).
38. M. H. Dominguez, A. E. Ayoub, P. Rakic, *Cereb. Cortex* 23, 2632 (November, 2013).

39. B. J. Molyneaux, P. Arlotta, J. R. L. Menezes, J. D. Macklis, *Nat. Rev. Neurosci.* 8, 427 (June, 2007).
40. J. Struyf, S. Dobrin, D. Page, *BMC Genomics* 9, (November, 2008).
41. T. R. Golub et al., *Science* 286, 531 (October, 1999).
42. V. N. Vapnik, *Statistical Learning Theory.* (Wiley, New York, 1998), pp. 736.
43. C. Cortes, V. Vapnik, *Mach. Learn.* 20, 273 (September, 1995).
44. T. S. Furey et al., *Bioinformatics* 16, 906 (October, 2000).
45. M. Moors et al., *Environ. Health Perspect.* 117, 1131 (July, 2009).
46. N. C. Kleinstreuer et al., *Nat. Biotechnol.* 32, 583 (June, 2014).
47. M. S. Wilson, J. R. Graham, A. J. Ball, *Neurotoxicology* 42, 33 (May, 2014).
48. N. V. Balmer, M. Leist, *Basic Clin. Pharmacol Toxicol.* 115, 59 (July, 2014).
49. H. Olson et al., *Regulatory Toxicology and Pharmacology* 32, 56 (2000).
50. S. Rakic, N. Zecevic, *Cereb. Cortex* 13, 1072 (October, 2003).
51. T. Kadoshima et al., *Proc. Natl. Acad. Sci. U S. A.* 110, 20284 (December, 2013).
52. G. K. Chen et al., *Nat. Methods* 8, 424 (May, 2011).
53. X. J. Li et al., *Development* 136, 4055 (December, 2009).
54. S. M. Chambers et al., *Nat. Biotechnol.* 27, 275 (March, 2009).
55. H. Nagase, G. B. Fields, *Biopolymers* 40, 399 (1996).
56. M. D. Pierschbacher, E. Ruoslahti, *Nature* 309, 30 (1984).
57. B. Langmead, C. Trapnell, M. Pop, S. L. Salzberg, *Genome Biol* 10, R25 (2009).
58. B. Li, C. N. Dewey, *BMC Bioinformatics* 12, 323 (2011).

TABLE 3

| | | NPCs, ECs, MCs w/PM | | NPCs, ECs, MCs | | NPCs, ECs, MCs | | NPCs ONLY (Control) |
|---|---|---|---|---|---|---|---|---|
| | | | | w/o PMs | with PMs | w/o PMs | with PMs | |
| | Day | Day 16 | Day 21 | Day 14 | | Day 21 | | |
| Gene.ID | | 3D Tox Experiment | | QC Experiment | | | | |
| GAPDH | | 3678.1 | 4299.3 | 7431.1 | 8239.2 | 5675.7 | 5720.6 | 6737.1 |
| *Glial* | | | | | | | | |
| GFAP | | 149.4 | 131.9 | 100.6 | 173.6 | 143.5 | 161.5 | 48.9 |
| S100B | | 259.7 | 161.5 | 201.5 | 281.3 | 139.2 | 212.3 | 99.4 |
| CD44 | | 179.9 | 299.2 | 228.5 | 210.7 | 285.3 | 314.5 | 317.3 |
| SLC1A3 (GLAST; Astrocytes, Bergman Glia) | | 635.4 | 455.0 | 315.2 | 294.2 | 339.1 | 369.8 | 274.5 |
| PDGFRA | | 3.7 | 2.8 | 7.1 | 4.1 | 2.5 | 3.3 | 1.2 |
| CLDN11 | | 3.0 | 3.1 | 9.0 | 12.2 | 4.9 | 5.8 | 9.3 |
| MAL | | 5.1 | 3.3 | 12.8 | 19.4 | 6.4 | 8.3 | 11.7 |
| MBP | | 3.5 | 4.2 | 1.2 | 2.1 | 2.2 | 2.5 | 1.6 |
| DLL1 | | 28.7 | 19.5 | 38.8 | 19.4 | 28.5 | 23.2 | 17.5 |
| FOXM1 | | 17.8 | 13.5 | 39.9 | 42.1 | 27.3 | 27.3 | 11.0 |
| TMPO | | 138.7 | 77.9 | 59.1 | 67.1 | 52.1 | 63.0 | 49.0 |
| *Microglia* | | | | | | | | |
| A1F1 (IBA1) | | 12.1 | 15.6 | 0.3 | 17.3 | 0.0 | 10.2 | 0.0 |
| ITGAM (Cd11b) | | 2.3 | 1.2 | 0.0 | 0.5 | 0.0 | 0.9 | 0.0 |
| PTPRC (CD45) | | 4.1 | 3.6 | 0.1 | 2.6 | 0.1 | 1.1 | 0.0 |
| CD68 | | 17.3 | 23.8 | 6.4 | 32.7 | 6.4 | 23.1 | 7.8 |
| CD86 | | 3.6 | 2.9 | 0.0 | 4.2 | 0.0 | 1.6 | 0.0 |
| CD14 | | 1.8 | 3.0 | 0.0 | 21.4 | 0.5 | 7.3 | 0.4 |
| CD4 | | 3.8 | 3.2 | 2.0 | 12.4 | 2.1 | 4.8 | 0.9 |
| TREM2 (Resting MG, strong cortex) | | 6.7 | 7.0 | 0.0 | 7.9 | 0.0 | 3.8 | 0.0 |
| *Neural General* | | | | | | | | |
| MAP2 | | 779.9 | 684.3 | 271.6 | 205.3 | 293.3 | 268.5 | 310.8 |
| CDH2 | | 777.6 | 665.9 | 338.8 | 256.8 | 300.1 | 298.9 | 235.5 |
| ACHE | | 22.6 | 20.2 | 32.0 | 36.6 | 52.4 | 57.0 | 50.9 |
| SLC18A3 (vesicular acetylcholine transporter) | | 1.9 | 1.7 | 0.9 | 0.7 | 1.3 | 0.8 | 1.1 |
| TPH1 | | 1.0 | 0.4 | 1.0 | 0.5 | 0.4 | 0.7 | 0.8 |
| TH | | 5.5 | 5.8 | 10.8 | 14.7 | 12.9 | 10.9 | 16.8 |
| NEUROG2 (Ngn2) | | 71.7 | 55.6 | 84.7 | 64.5 | 51.8 | 62.4 | 78.9 |
| ISL1 | | 5.9 | 3.3 | 2.0 | 2.4 | 3.5 | 4.6 | 5.0 |
| *GABAergic* | | | | | | | | |
| GAD1 | | 11.5 | 31.6 | 12.7 | 7.0 | 22.1 | 17.3 | 28.9 |
| GAD2 | | 1.8 | 2.9 | 2.3 | 3.0 | 3.7 | 4.2 | 4.5 |
| SLC6A1 (GABA transporter 1) | | 9.8 | 12.5 | 5.2 | 2.8 | 13.4 | 10.4 | 9.2 |
| CALB2 (CalRet) | | 111.7 | 156.4 | 171.3 | 147.8 | 214.9 | 219.4 | 204.9 |
| ASCL1 (MASH1) | | 20.8 | 14.3 | 31.4 | 10.1 | 26.6 | 15.5 | 11.3 |

TABLE 3-continued

| | | | Averaged Expression Data for Markers of Vascular, Neuronal, and Glial Cell Types | | | | |

| | | NPCs, ECs, MCs w/PM | | NPCs, ECs, MCs | | NPCs, ECs, MCs | | NPCs ONLY (Control) |
|---|---|---|---|---|---|---|---|---|
| | | | | w/o PMs | with PMs | w/o PMs | with PMs | |
| | Day | Day 16 | Day 21 | Day 14 | | Day 21 | | |

| Glutamatergic | | | | | | | |
|---|---|---|---|---|---|---|---|
| SLC32A1 (VGAT) | 1.0 | 2.0 | 0.6 | 0.5 | 0.7 | 1.0 | 1.0 |
| GLUL (glutamate-ammonia ligase) | 137.7 | 285.3 | 95.4 | 117.7 | 154.2 | 170.2 | 229.7 |
| SLC17A7 (VGLUT1) | 0.6 | 0.8 | 1.4 | 1.1 | 3.4 | 2.2 | 3.9 |
| SLC17A6 (VGLUT2) | 93.5 | 110.0 | 48.0 | 35.9 | 85.8 | 74.9 | 95.9 |
| SLC17A8 (VGLUT3) | 10.6 | 14.7 | 6.9 | 5.5 | 9.0 | 8.1 | 5.1 |
| SLC1A1 (glial high affinity glutamate transporter) | 4.9 | 7.0 | 4.3 | 2.2 | 4.8 | 3.8 | 3.4 |
| SLC1A2(neuronal/epithelial high affinity glutamate transporter) | 103.2 | 93.4 | 37.1 | 31.6 | 52.0 | 33.7 | 39.9 |
| Transporter and Vesicle proteins | | | | | | | |
| SV2A | 90.9 | 77.1 | 92.3 | 96.7 | 115.3 | 105.1 | 122.9 |
| SV2B | 2.2 | 3.4 | 1.1 | 1.0 | 3.4 | 2.3 | 2.7 |
| SV2C | 10.5 | 4.1 | 2.4 | 1.7 | 3.3 | 2.5 | 1.6 |
| SNAP25 | 95.3 | 112.3 | 65.7 | 56.3 | 96.2 | 98.4 | 117.6 |
| CBLN1 (Cerebellin-1) | 34.7 | 36.7 | 24.0 | 21.7 | 38.5 | 39.9 | 40.9 |
| CBLN2 | 14.2 | 13.9 | 7.0 | 7.5 | 8.3 | 6.8 | 7.5 |
| CBLN3 | 1.2 | 1.3 | 2.3 | 2.6 | 2.3 | 2.9 | 3.3 |
| CBLN4 | 6.1 | 6.5 | 1.8 | 1.1 | 3.9 | 2.3 | 3.3 |
| DLG4 (PSD-95) | 101.2 | 140.7 | 118.4 | 85.2 | 168.7 | 150.3 | 165.6 |
| SYP (synaptophysin) | 44.6 | 54.6 | 64.0 | 63.5 | 100.9 | 112.0 | 113.2 |
| SYN1 (synapsin I) | 26.6 | 32.4 | 22.9 | 23.7 | 42.7 | 53.2 | 46.0 |
| SYN2 | 7.5 | 14.1 | 3.6 | 3.4 | 9.7 | 8.7 | 8.0 |
| SYN3 | 3.3 | 5.9 | 4.4 | 1.5 | 10.7 | 12.3 | 10.1 |
| Blood Vessel (EC or MC) | | | | | | | |
| PECAM1/CD31 | 1.4 | 1.7 | 2.1 | 4.1 | 1.4 | 2.1 | 1.0 |
| CD34 | 22.8 | 12.7 | 40.9 | 70.9 | 18.1 | 31.5 | 28.0 |
| MCAM | 15.7 | 23.8 | 36.9 | 33.9 | 39.0 | 42.0 | 51.1 |
| KDR/VEGFR2/FLK1 | 9.2 | 8.7 | 13.0 | 25.8 | 7.8 | 11.5 | 11.4 |
| VEGFA | 512.8 | 890.2 | 623.5 | 294.7 | 677.6 | 829.1 | 732.8 |
| PDGFRB | 10.5 | 12.1 | 40.2 | 30.4 | 37.2 | 32.2 | 15.6 |
| PDGFB | 24.8 | 14.2 | 32.7 | 41.4 | 20.9 | 21.9 | 30.0 |
| ANPEP | 2.1 | 1.5 | 3.6 | 7.1 | 2.1 | 3.8 | 2.4 |
| CSPG4 | 1.9 | 1.7 | 11.9 | 12.1 | 12.3 | 10.8 | 8.8 |
| ACTA2 | 30.8 | 88.9 | 254.4 | 181.2 | 168.2 | 240.3 | 143.4 |
| CDH5 | 2.0 | 0.3 | 4.5 | 5.0 | 1.9 | 2.6 | 1.1 |
| SLC2A1 | 95.0 | 139.6 | 262.0 | 66.2 | 129.7 | 98.3 | 133.7 |
| AQP1 | 5.1 | 9.5 | 11.6 | 18.6 | 17.1 | 25.5 | 6.6 |
| GPR124 | 1.2 | 1.2 | 17.8 | 13.0 | 6.7 | 8.6 | 1.5 |
| AQP4 | 64.6 | 52.8 | 29.5 | 31.2 | 32.3 | 29.4 | 39.4 |
| NPC | | | | | | | |
| NES | 1275.2 | 763.9 | 620.7 | 895.9 | 562.5 | 642.7 | 625.1 |
| VIM | 5871.3 | 8872.8 | 13171.0 | 9312.2 | 15142.8 | 13388.9 | 14840.7 |
| EOMES/Tbr2 | 1.6 | 2.2 | 3.5 | 3.3 | 3.1 | 3.7 | 4.3 |
| PAX6 | 3.7 | 2.6 | 1.7 | 1.6 | 1.9 | 2.2 | 2.0 |
| SOX1 | 75.2 | 53.9 | 34.4 | 40.6 | 33.2 | 40.1 | 22.4 |
| SOX2 | 138.5 | 160.7 | 247.4 | 184.8 | 249.3 | 341.0 | 202.7 |
| SOX9 | 169.3 | 153.2 | 106.7 | 62.9 | 110.9 | 133.6 | 87.6 |
| NEUROD1 | 14.0 | 16.6 | 7.6 | 5.5 | 6.1 | 9.1 | 11.9 |
| NOTCH1 | 82.7 | 81.0 | 153.2 | 95.9 | 173.7 | 129.0 | 128.1 |
| NOTCH2 | 51.1 | 40.7 | 46.6 | 38.1 | 53.9 | 40.8 | 45.4 |
| NR2F1 (COUP-TF1) | 51.9 | 48.6 | 40.1 | 35.9 | 42.5 | 43.4 | 32.5 |
| Cortical | | | | | | | |
| RELN | 72.9 | 45.1 | 58.3 | 35.6 | 50.6 | 31.4 | 44.7 |
| CUX1 | 54.0 | 54.0 | 57.7 | 46.1 | 60.0 | 65.6 | 52.9 |
| CUX2 | 18.7 | 14.6 | 23.0 | 21.1 | 26.4 | 27.9 | 26.3 |
| SATB1 | 72.5 | 56.5 | 43.7 | 24.3 | 49.0 | 49.1 | 41.3 |
| SATB2 | 10.1 | 8.3 | 7.6 | 7.1 | 7.7 | 8.0 | 8.2 |
| RORB | 3.0 | 1.9 | 1.5 | 0.7 | 3.1 | 2.3 | 1.3 |
| BCL11B/Ctip2 | 37.4 | 34.1 | 11.5 | 8.5 | 12.4 | 9.0 | 11.4 |
| SOX5 | 13.5 | 5.9 | 9.9 | 5.3 | 8.3 | 7.1 | 6.7 |
| POU3F1/SCIP | 7.4 | 6.5 | 7.9 | 10.1 | 7.1 | 8.9 | 7.4 |
| FOXP1 | 30.1 | 29.6 | 22.8 | 19.5 | 16.8 | 18.4 | 15.7 |
| FOXP2 | 34.5 | 27.3 | 33.7 | 19.2 | 25.2 | 32.7 | 24.1 |
| ETV1 | 19.1 | 18.2 | 11.4 | 7.1 | 10.4 | 11.6 | 9.5 |
| MAP1B | 1001.4 | 782.1 | 460.8 | 349.1 | 454.6 | 375.1 | 429.3 |
| TLE4 | 43.3 | 48.4 | 47.6 | 33.0 | 37.2 | 36.8 | 44.9 |

TABLE 3-continued

Averaged Expression Data for Markers of Vascular, Neuronal, and Glial Cell Types

| | | NPCs, ECs, MCs w/PM | | NPCs, ECs, MCs w/o PMs   with PMs | | NPCs, ECs, MCs w/o PMs   with PMs | | NPCs ONLY (Control) |
|---|---|---|---|---|---|---|---|---|
| | Day | Day 16 | Day 21 | Day 14 | | Day 21 | | |
| POU3F2/Bm2 | | 160.9 | 122.6 | 118.0 | 82.3 | 122.6 | 121.2 | 96.5 |
| FOXO1 | | 1.6 | 2.0 | 4.3 | 2.6 | 2.5 | 1.9 | 2.3 |
| LIX1 | | 5.1 | 3.9 | 4.7 | 2.9 | 6.5 | 3.9 | 3.7 |
| SYT9 | | 35.7 | 22.5 | 19.9 | 17.0 | 25.0 | 25.8 | 18.9 |
| S100A10 | | 117.2 | 124.3 | 344.4 | 458.2 | 215.5 | 308.7 | 268.4 |
| OMA1 | | 11.3 | 14.8 | 9.8 | 6.9 | 11.6 | 10.5 | 9.0 |
| LDB2 | | 33.0 | 39.3 | 37.0 | 22.1 | 38.4 | 44.1 | 33.0 |
| CRIM1 | | 42.6 | 36.7 | 32.5 | 23.8 | 27.8 | 24.6 | 29.5 |
| PCP4 | | 5.5 | 8.3 | 5.2 | 3.3 | 11.0 | 9.7 | 12.6 |
| RAC3 | | 52.7 | 60.9 | 133.5 | 158.5 | 152.2 | 166.3 | 169.2 |
| CRYM | | 4.2 | 4.9 | 2.7 | 3.1 | 1.3 | 2.3 | 3.2 |
| IGFBP4 | | 10.5 | 17.8 | 54.6 | 50.9 | 42.2 | 48.2 | 28.7 |
| DKK3 | | 409.7 | 388.8 | 1003.0 | 803.8 | 1185.8 | 1219.9 | 752.7 |
| SEMA3E | | 3.6 | 3.5 | 4.4 | 3.6 | 2.6 | 3.0 | 2.9 |
| NR4A3 | | 3.5 | 2.7 | 1.3 | 0.8 | 1.1 | 1.6 | 1.4 |
| LXN | | 4.5 | 1.8 | 14.2 | 13.9 | 7.4 | 12.2 | 2.2 |
| ID2 | | 120.1 | 227.6 | 242.1 | 115.5 | 202.2 | 188.7 | 132.2 |
| SLITRK1 | | 12.6 | 14.7 | 5.4 | 6.2 | 5.2 | 5.4 | 6.6 |
| LMO3 | | 5.6 | 6.8 | 2.0 | 1.2 | 4.0 | 3.0 | 3.5 |
| LMO4 | | 73.0 | 101.2 | 65.5 | 56.9 | 100.2 | 78.7 | 101.1 |
| CTGF | | 127.1 | 112.5 | 330.6 | 173.2 | 123.6 | 95.9 | 143.8 |
| Ependyma/Neuroepithelium (early) | | | | | | | | |
| M1 (CD133) | | 92.7 | 97.9 | 55.8 | 47.5 | 70.0 | 68.0 | 47.6 |
| ITGA6 | | 77.1 | 56.3 | 26.6 | 22.6 | 23.0 | 20.7 | 30.8 |

NPC = neural progenitor cells;
ECs = endothelial cells;
MCs = mesenchymal cells;
PM = primitive macrophages

We claim:

1. A method of producing a chemically defined, xenogen-free vascularized neural tissue construct, comprising:

(a) seeding a xenogen-free, three-dimensional (3D), RGD-containing peptide-functionalized, matrix metalloproteinase (MMP)-degradable, porous hydrogel with human pluripotent stem cell-derived neural progenitor cells;

(b) culturing the seeded hydrogel under chemically defined, xenogen-free conditions for a length of time sufficient to detect differentiation of at least a portion of the neural progenitor cells;

(c) dispersing, on or within the cultured seeded hydrogel, human endothelial cells and human mesenchymal cells; and (d) culturing the seeded hydrogel comprising the dispersed human endothelial cells and human mesenchymal cells under chemically defined, xenogen-free culture conditions that promote cell differentiation, whereby a 3D chemically defined, xenogen-free, vascularized neural tissue construct comprising stratified layers of human neurons and glial cells is produced within about 14 days from seeding step (a).

2. The method of claim 1 comprising, in step (c), further dispersing, on or within the cultured seeded material, one or more of primitive macrophages and pericytes.

3. The method of claim 1, wherein the hydrogel comprises polymerized poly (ethylene glycol) (PEG) or polymerized polysaccharide.

4. The method of claim 1, wherein the dispersed human endothelial cells are derived under chemically defined, xenogen-free conditions from a human pluripotent stem cell.

5. The method of claim 4, wherein the human pluripotent stem cell is an embryonic stem cell or an induced pluripotent stem cell.

6. The method of claim 1, wherein the seeded material comprising the dispersed human endothelial cells further comprises human pluripotent stem cell-derived primitive macrophages and wherein the three-dimensional vascularized neural tissue construct comprises mature microglia.

7. The method of claim 1, wherein seeding the porous material comprises contacting to the porous material at least one human neural progenitor cell.

8. The method of claim 1 further comprising dispersing within or on the porous material a bioactive agent that modulates a morphological feature, function, or differentiation status of a cell seeded or dispersed therein.

9. The method of claim 8, wherein the bioactive agent is selected from the group consisting of a growth factor, a cytokine, and a bioactive peptide, or a combination thereof.

10. The method of claim 1, wherein the vascularized neural tissue construct exhibits one or more properties selected from the group consisting of: (i) an interconnected vasculature; (ii) differentiated cells within the neural tissue construct mutually contact each other in three dimensions; (iii) more than one layer of cells; and (iv) a function or property characteristic of human neural tissue in vivo or in situ.

11. The method of claim 1, wherein the neurons and glial cells are selected from the group consisting of GABAergic neurons, glutamatergic neurons, astrocytes, and oligodendrocytes.

12. A three-dimensional (3D) vascularized neural tissue construct obtained according to the method of claim 1.

13. The neural tissue construct of claim 12, comprising mature microglia.

14. The neural tissue construct of claim 12, comprising stratified layers of neurons and glia.

15. The method of claim 1, wherein the dispersed human mesenchymal cells are derived under chemically defined, xenogen-free conditions from a human pluripotent stem cell.

16. The method of claim 15, wherein the human pluripotent stem cell is an embryonic stem cell or an induced pluripotent stem cell.

* * * * *